(12) United States Patent
Yodfat et al.

(10) Patent No.: US 8,628,500 B2
(45) Date of Patent: *Jan. 14, 2014

(54) PROTECTOR APPARATUS

(75) Inventors: Ofer Yodfat, Maccabim-Reut (IL); Avraham Neta, Misgav (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/136,291

(22) Filed: Jul. 27, 2011

(65) Prior Publication Data

US 2011/0288390 A1 Nov. 24, 2011

Related U.S. Application Data

(63) Continuation of application No. 12/215,219, filed on Jun. 25, 2008, now Pat. No. 8,002,752.

(60) Provisional application No. 60/937,155, filed on Jun. 25, 2007, provisional application No. 60/937,214, filed on Jun. 25, 2007, provisional application No. 60/937,163, filed on Jun. 25, 2007.

(51) Int. Cl.
*A61M 5/32* (2006.01)

(52) U.S. Cl.
USPC ............ 604/198; 604/192; 604/272; 604/180

(58) Field of Classification Search
USPC ................. 604/164.01–170.03, 136
See application file for complete search history.

(56) References Cited

U.S. PATENT DOCUMENTS

| | | | |
|---|---|---|---|
| 3,396,726 A | 8/1968 | Sarnoff | 604/138 |
| 4,755,173 A | 7/1988 | Konopka et al. | 604/167 |
| 5,176,662 A | 1/1993 | Bartholomew et al. | 604/283 |
| 5,257,980 A | 11/1993 | Van Antwerp et al. | 604/282 |
| 5,390,671 A | 2/1995 | Lord et al. | 128/635 |
| 5,568,806 A | 10/1996 | Cheney, II et al. | 128/635 |

(Continued)

FOREIGN PATENT DOCUMENTS

| | | |
|---|---|---|
| WO | WO 99/33504 | 7/1999 |
| WO | WO-2005046781 A1 | 5/2005 |

(Continued)

OTHER PUBLICATIONS

International Search Report for PCT application No. PCT/IL2008/000859.

(Continued)

*Primary Examiner* — Kevin C Sirmons
*Assistant Examiner* — Brandy S Lee
(74) *Attorney, Agent, or Firm* — Mintz Levin Cohn Ferris Glovsky and Popeo, PC

(57) ABSTRACT

An apparatus and a method for use with a device for delivery of a therapeutic fluid into a body of a patient and/or for sensing of a bodily analyte are disclosed. The apparatus is adapted for accommodating at least one subcutaneously insertable element and at least one penetrating member for penetrating the skin of the patient. The apparatus includes a protective member having an elongate body from which the subcutaneously insertable element and the penetrating member can be protracted to penetrate the skin of the patient and into which the penetrating member can be retracted subsequent to the penetrating, thereby retaining the subcutaneously insertable element in the body of the patient.

21 Claims, 34 Drawing Sheets

(56) References Cited

U.S. PATENT DOCUMENTS

| | | | |
|---|---|---|---|
| 5,586,553 | A | 12/1996 | Halili et al. ............... 128/635 |
| 6,093,172 | A | 7/2000 | Funderburk et al. .......... 604/135 |
| 6,143,164 | A | 11/2000 | Heller et al. ............... 295/777.5 |
| 6,254,586 | B1 * | 7/2001 | Mann et al. ................. 604/506 |
| 6,699,218 | B2 | 3/2004 | Flaherty et al. .............. 604/131 |
| 6,830,562 | B2 | 12/2004 | Mogensen et al. ....... 604/164.12 |
| 7,110,803 | B2 | 9/2006 | Shults et al. ................. 600/347 |
| 2003/0100862 | A1 | 5/2003 | Edwards et al. ............. 604/138 |
| 2004/0158207 | A1 * | 8/2004 | Hunn et al. .............. 604/164.01 |
| 2005/0101932 | A1 | 5/2005 | Cote et al. ................... 604/506 |
| 2006/0020189 | A1 | 1/2006 | Brister et al. ................ 600/345 |
| 2007/0093754 | A1 | 4/2007 | Mogensen et al. ....... 604/164.01 |
| 2007/0191702 | A1 | 8/2007 | Yodfat et al. ................. 600/365 |
| 2008/0097481 | A1 | 4/2008 | Schorr et al. ................. 606/144 |
| 2008/0214916 | A1 | 9/2008 | Yodfat et al. ................. 600/347 |
| 2008/0215035 | A1 | 9/2008 | Yodfat et al. ................. 604/513 |
| 2008/0281290 | A1 | 11/2008 | Yodfat et al. ................. 604/504 |
| 2008/0319414 | A1 | 12/2008 | Yodfat et al. ................. 604/506 |
| 2009/0163867 | A1 | 6/2009 | Marshall et al. ............. 604/136 |
| 2009/0198215 | A1 | 8/2009 | Chong et al. ................. 604/506 |

FOREIGN PATENT DOCUMENTS

| | | |
|---|---|---|
| WO | WO 2007/093981 | 8/2007 |
| WO | WO 2008/012817 | 1/2008 |
| WO | WO 2008/029403 | 3/2008 |
| WO | WO 2008/038274 | 4/2008 |
| WO | WO 2008/065646 | 6/2008 |
| WO | WO 2008/078318 | 7/2008 |
| WO | WO 2008/078319 | 7/2008 |
| WO | WO 2009/001345 | 12/2008 |
| WO | WO 2009/056981 | 5/2009 |

OTHER PUBLICATIONS

Amendment and Response filed on Sep. 27, 2010 for U.S. Appl. No. 12/215,255 (22 pgs.).

Final Office Action mail date May 27, 2010 for U.S. Appl. No. 12/215,255 (15 pgs.).

Amendment and Response Filed on Feb. 9, 2010 for U.S. Appl. No. 12/215,255 (20 pgs.).

Non-Final Office Action mail date Sep. 9, 2009 for U.S. Appl. No. 12/215,255 (16 pgs.).

Amendment and Response field on Jul. 20, 2009 for U.S. Appl. No. 12/215,255 (10 pgs.).

Office Action mail date May 29, 2009 for U.S. Appl. No. 12/215,255 (6 pgs).

* cited by examiner

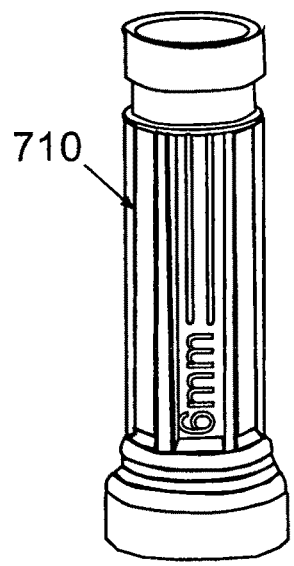
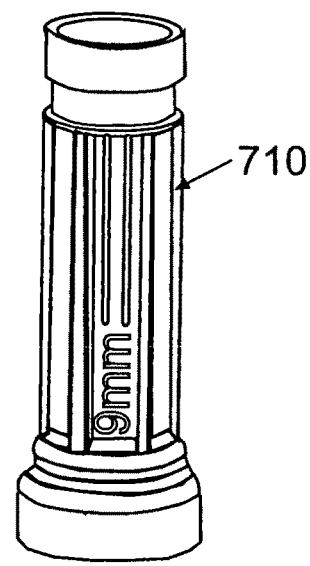
Fig. 11a    Fig. 11c
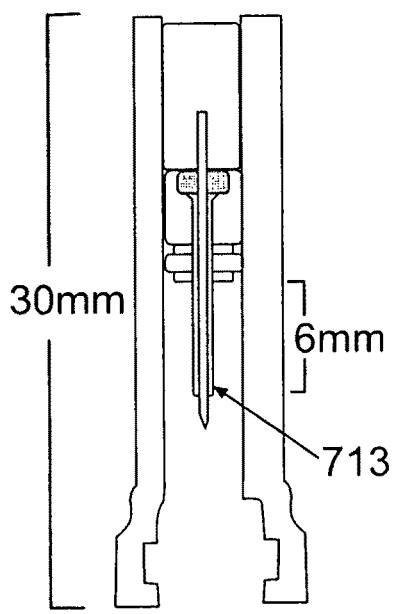
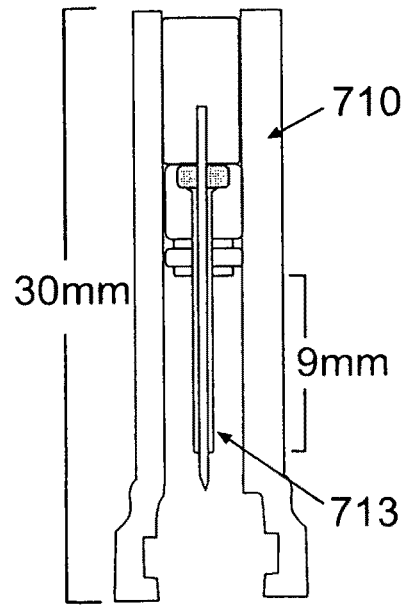
Fig. 11b    Fig. 11d

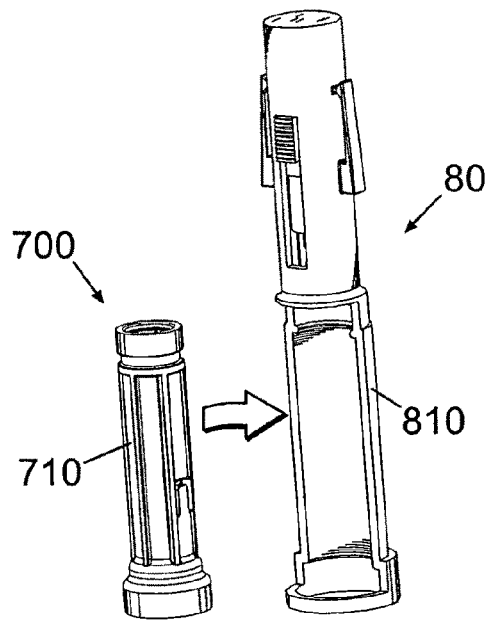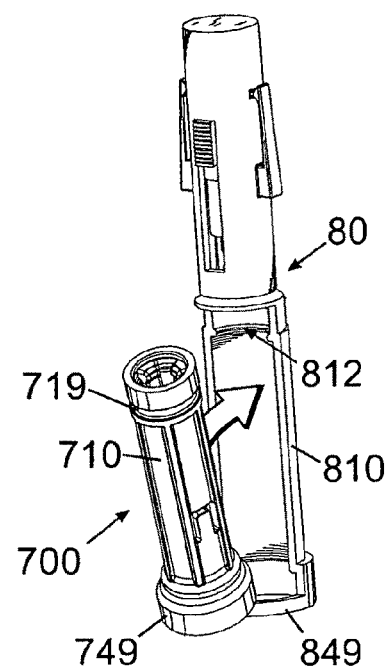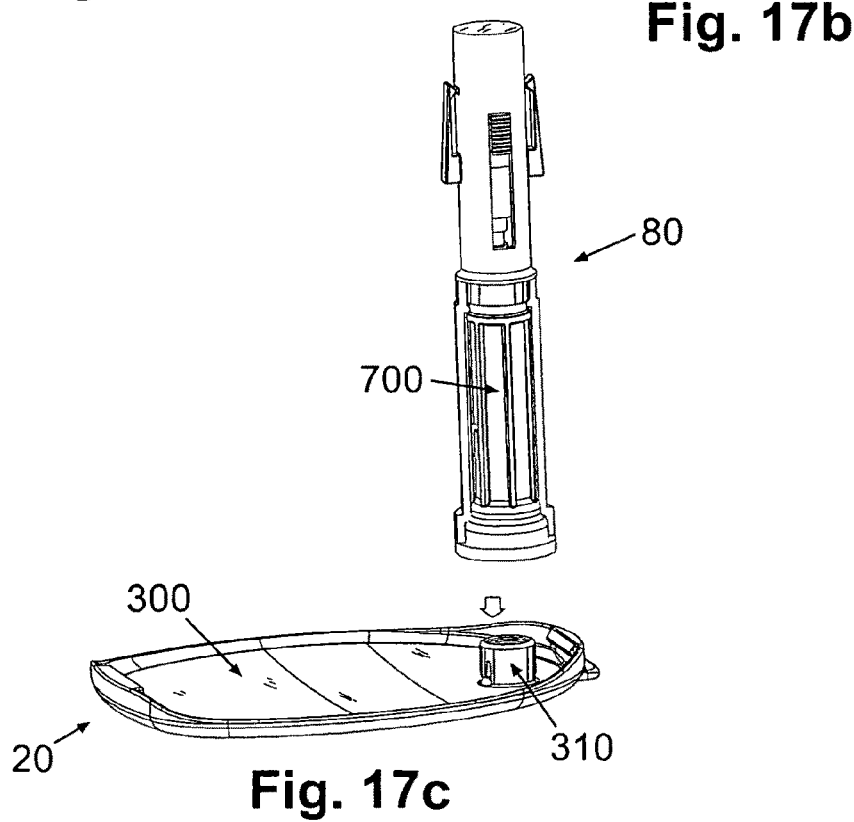
Fig. 17a
Fig. 17b
Fig. 17c

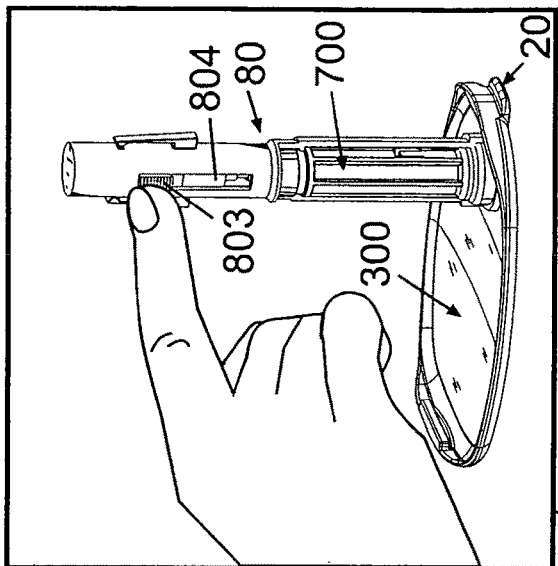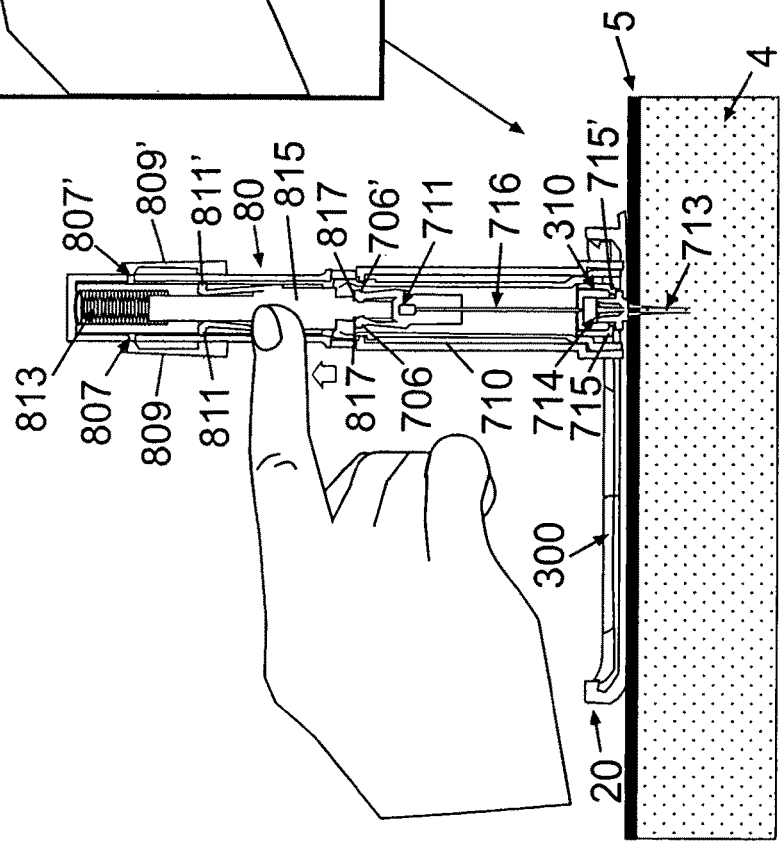

PROTECTOR APPARATUS

CROSS-REFERENCE TO RELATED APPLICATIONS

The present application is a continuation of U.S. patent application Ser. No. 12/215,219, filed on Jun. 25, 2008, which claims priority to U.S. Provisional Patent Application No. 60/937,155, entitled "Protector for Cannula and Penetrating Member Insertable in the Body of a Patient", U.S. Provisional Patent Application No. 60/937,214, entitled "Insertion Device for Inserting a Cannula into a Body", and U.S. Provisional Patent Application No. 60/937,163, entitled "Devices and Methods for Pain Reduction", all filed on Jun. 25, 2007, the disclosures of which are incorporated herein by reference in their entireties.

FIELD OF THE INVENTION

Embodiments of the present invention generally relate to medical devices, and more particularly to devices that administer medication into the body of a patient and/or sense analyte level(s) in a bodily fluid. Even more particularly, embodiments of the present invention relate to protection of a cannula cartridge unit that contains a cannula for delivery of a drug by an infusion pump and/or for continuous sensing of a body analyte. In some embodiments, the cannula cartridge unit contains a cannula for delivery of a drug, and/or a sensor for continuous sensing of a body analyte, which can be accommodated in a skin adherable patch unit. Some embodiments of the present invention also relate to a method for manual, semi-automatic and/or fully automatic insertion of a cannula into the body.

BACKGROUND OF THE INVENTION

Continuous subcutaneous delivery of medication or monitoring of a body analyte is often accomplished using a cannula, which remains in the body of a patient for several days. Diabetes patients may use such cannula positioned in a subcutaneous compartment for continuous delivery of insulin effectuated by pumps and/or for monitoring interstitial glucose levels by means of sensors. A combination of a tube, connecting an insulin pump to the cannula and a detachable connector is often referred to as an infusion set. Such infusion sets and modes of their insertion are discussed in, for example, U.S. Pat. Nos. 4,755,173, 5,176,662 and 5,257,980. Subcutaneous cannula insertion modes for continuous glucose monitoring are discussed in, for example, U.S. Pat. Nos. 5,390,671, 5,568,806 and 5,586,553. Usually transcutaneous ("hypodermic") cannula insertion can be carried out with the aid of a sharp metallic "penetrating member" to be withdrawn after piercing the skin. This procedure can be carried out manually by the patient. The insertion is usually painful and may require considerable skill. Some patients are reluctant or hesitant to pierce their own skin, and therefore achieving proper insertion of the cannula may be difficult. Another hurdle of currently existing methods of manual or automatic cannula insertion is a possibility for unintentional self piercing. Conventional systems have a further problem associated with a need for a proper bio-hazard disposal of the cannula. Such difficulties can be attributable to insufficient patient's manual dexterity or alternatively to his or her anxiety associated with anticipated discomfort as the needle pierces the skin. This problem can be especially significant when an insulin pump is used since misplacement of the cannula can cause kinking along the cannula, incorrect cannula insertion angle or incorrect cannula insertion depth leading eventually to cannula obstruction. As a result of this, delivery of insulin could be hampered causing a life threatening situation.

In an attempt to cope with this problem, automatic infusion set insertion devices ("inserters") were developed to assure correct placement of a cannula in the body of the patient (i.e., subcutaneous layer), at a correct angle, while minimizing pain and hazardous obstructions associated with cannula insertion. U.S. Pat. Nos. 6,093,172 and 6,830,562 disclose inserters having a spring-loaded plunger for an automatic subcutaneous placement of infusion sets. These automatic inserters can be used with "pager like" insulin infusion pumps having long tubing and a cannula. However, these devices cannot be used for insertion of a cannula that is employed in skin adherable insulin pumps, which do not employ long external tubing. An example of such device is disclosed in U.S. Pat. No. 6,699,218 to Flaherty et al. In this skin adherable insulin delivery device, the cannula is rigidly connected to the pump's housing. After adhesion of the device to user's skin, the cannula is fired, i.e., it emerges from the device's housing and pierces the skin. Consecutively, the penetrating member is retracted back into the pump's housing.

One of the disadvantages of this device is that it is relatively bulky, heavy and indiscreet because the spring loaded mechanism is enclosed within the device's housing during the entire period of usage. In addition, the cannula has only one length, and it can penetrate the skin at only a certain angle. Further, the patient cannot adjust these parameters according to various insertion sites and other clinical requirements.

Continuous glucose monitors are disclosed in U.S. Pat. Nos. 5,390,671 and 6,143,164, assigned to MiniMed and E. Heller & Company, respectively. These devices monitor glucose levels within the subcutaneous compartment by a sensor that is insertable manually or automatically, as discussed in U.S. Pat. No. 7,110,803, assigned to DexCom, in a similar manner as is inserted a cannula for drug delivery.

In view of the foregoing, it would be desirable to provide improved systems and methods for protecting and concealing needles for use in inserting cannulae and/or sensors into the body of a patient.

SUMMARY OF THE INVENTION

Some embodiments of the present invention provide a cannula cartridge unit that contains cannula, penetrating member and protector. The cannula and penetrating member are concealed and guarded by the protector (e.g., a housing). For example, the protector may include an elongate body having a longitudinal axis and a first end configured to mate with a patch secured cutaneously to a human body. During insertion, the cannula and penetrating member are fired from the protector (e.g., along the longitudinal axis). The cannula remains in the body and the penetrating member is retracted back into the protector. Thereafter, the penetrating member and the protector may be discarded.

The cannula cartridge unit can be loaded into an inserter for precise placement of a cannula within the body of a user. The inserter may be configured for automatic insertion of a cannula that is used with the fluid delivery pump. The pump may be a remote-controlled skin adherable patch type (e.g., a dispensing patch unit) allowing programmed fluid delivery and can include a continuous analyte level monitor. In some embodiments, the delivered fluid is insulin and the monitored analyte is glucose. In some embodiments, the device includes a remote control unit and the following three units:

1. A dispensing patch unit including:
   a. a reusable part containing driving mechanism, printed circuit board ("PCB") and electronics;
   b. a disposable part containing a reservoir, a delivery tube and an outlet port with a connecting lumen;
2. A cradle unit for connecting and re-connecting the dispensing patch unit to the body of the patient. The cradle unit includes a passage (i.e., designed as a "well") to allow cannula penetration into the skin and an adhesive layer underneath its lower face to allow attachment to the body.
3. A cannula cartridge unit including a cannula, a penetrating member, and a protector. A cannula hub contains a self-sealable rubber septum that can be repeatedly pierced by a connecting lumen provided in the disposable part of the dispensing patch unit.

System set-up may be accomplished in the following sequence:
1. Reservoir filling
2. Dispensing patch unit is assembled from two parts (disposable and reusable parts);
3. Cradle unit adhesion (in some embodiment this step is carried out after connecting an inserter to the cradle unit)
4. Cannula insertion:
   a. cannula cartridge unit is loaded into an inserter (in some embodiments this step is carried out after the inserter is connected to the cradle unit);
   b. inserter is connected to a cradle unit;
   c. cannula is automatically or manually advanced through the cradle unit towards the body, pierces the skin, penetrates it and resides in the subcutaneous compartment;
   d. penetrating member is automatically or manually withdrawn from the body into the protector and the cannula is rigidly secured at the cradle unit.
5. Dispensing patch unit is connected to the cradle unit such that connecting lumen emerges from the disposable part's outlet port, pierces the cannula hub's rubber septum and maintains fluid communication between the reservoir, delivery tube, cannula and subcutaneous tissue.
6. Fluid delivery is programmed by a remote control unit.

In some embodiments the cannula delivering a fluid (e.g., insulin) includes a sensor for monitoring a body analyte in the body (e.g., glucose). Fluid delivery can be adjusted according to sensor inputs in a semi- or fully-closed-loop mode. In some embodiments, the dispensing patch unit can include both a cannula for fluid delivery and a sensor for analyte sensing, which can both be inserted into the body.

In some embodiments, a skin adherable infusion pump ("dispensing patch unit") is provided without tubing, where the dispensing patch unit is configured to be connected and disconnected to and from a cradle unit, and in which a cannula can be inserted through the cradle unit into the body and remain rigidly connected to the cradle unit.

In some embodiments, a skin adherable analyte monitoring device is provided that is configured to be connected and disconnected to and from a cradle unit. The device is further provided with a sensor that can be inserted through the cradle unit into the body and remain rigidly connected to the cradle unit.

In other embodiments, a skin adherable infusion pump and analyte monitoring device is provided that can be connected and disconnected to and from a cradle unit. The device employs one dual function cannula/sensor that can be inserted through the cradle unit into the body and remain rigidly connected to the cradle unit.

Some embodiments of the present invention also provide one or more of the following features:

The cannula can be coupled with a penetrating member to facilitate skin pricking.

Cannula and penetrating member can be concealed and covered by a protective housing ("protector") to avoid unintentional pricking. The cannula, the penetrating member and the protector will altogether be referred to as a "cannula cartridge unit".

Cannula cartridge unit can be loadable into an automatic insertion means ("inserter").

Cannula and penetrating member can be fired together into the body by the inserter.

Penetrating member can be retractable back into protector and then they together will be disposed of.

In some embodiments, a cannula contained within a cannula cartridge unit can be automatically inserted into the body of the patient and can be used for delivery of medication to a patient by a dispensing patch unit.

In some embodiments, a sensor contained within a cannula cartridge unit is provided that can be suitable for continuous analyte monitoring (i.e., continuous glucose monitoring) and which can be adhered to a patient's skin.

In still other embodiments, a cannula contained within a cannula cartridge unit is provided that can be precisely aligned relative to a cradle unit and which can be rigidly connected to the cradle unit after insertion.

In some embodiments, the present invention provides a cannula contained within a cannula cartridge unit that can be used in connection with a skin adherable pump. In some embodiments, the present invention relates to a method for automatically inserting the cannula.

In some embodiments, the present invention provides a sensor contained within a cannula cartridge unit that can be used in connection with a skin adherable continuous analyte monitoring means. In some embodiments, the present invention relates to a method for automatically inserting the sensor.

Some embodiments of the present invention provide a cannula and a sensor contained within a cannula cartridge unit that is intended for use in association with a skin adherable pump having analyte sensing and fluid dispensing capabilities, where the fluid dispensing can be adjusted according to analyte sensing in a semi- or a fully-closed-loop mode.

In some embodiments, the present invention relates to a method for automatically inserting the cannula and the sensor, where the cannula is used for the insulin delivery and the sensor is used for continuously monitoring the glucose levels.

In some embodiments, the invention provides a cannula cartridge unit that can be loaded into an inserter and can be easily unloaded from the inserter. In some embodiments, the present invention provides a cannula cartridge unit that can be easily handled and has a griping mean for inserter loading and unloading.

Some embodiments of the present invention relate to a cannula or a sensor contained within a cannula cartridge unit and a method for automatically inserting the cannula or the sensor into the body of the user.

In some embodiments, the present invention provides a cannula cartridge unit loaded into an inserter that can automatically insert the cannula into the body of the user, where the retraction of the penetrating member can be performed manually.

In some embodiments, the inserter is preloaded with a cannula cartridge unit. After attaching the cradle unit to the skin of the user and connecting the loaded inserter to the cradle unit, the user presses a trigger provided in the inserter. The trigger releases a spring from its loaded position and a dedicated rod which is connected to the spring forcefully pushes the cannula and the penetrating needle out from the protector through the cradle unit's passage (i.e., "well") towards the body of the user. Consecutively, the penetrating member is manually retracted from the body of the user back into the protector and the cannula hub is rigidly connected to the well. Finally, the inserter is removed from the cradle unit and the protector (with the penetrating member inside) is unloaded and disposed of.

In some embodiments, the inserter is preloaded with the cannula cartridge unit and the cradle unit. After spring loading, the user attaches the cradle unit to the skin and pushes a release button. Insertion of the cannula and the penetrating member into the body and retraction of the penetrating member therefrom can be carried out automatically using a spring-loaded flywheel.

In some embodiments, the present invention provides a cannula cartridge unit that can be loaded into an inserter that enables alignment of the cannula with a cradle unit.

In some embodiments, the present invention provides a cannula cartridge unit that can be loaded into a disposable or reusable inserter. In the disposable inserter configuration, the inserter is preloaded with the cannula cartridge unit and, after insertion of the cannula, the protector (with the penetrating member inside) remains within the inserter's housing and the inserter is then discarded.

In some embodiments, the present invention provides a cannula cartridge unit that allows cannula insertion at any desired penetration angle.

In some embodiments, the present invention provides a cannula cartridge unit that allows insertion of a cannula at any desired depth, i.e., the patient can choose the desired cannula length.

In some embodiments, the present invention provides a cannula cartridge unit that can be directly attached to cradle unit and allows manual insertion. The cannula cartridge unit is attached to the cradle unit's passage ("well") and the cannula and the penetrating member are pushed into the body with the aid of a dedicated rod (or any other similar device). After insertion, the protector is removed from the cradle unit and the penetrating member is manually retracted from the body and is disposed of.

BRIEF DESCRIPTION OF THE DRAWINGS

For a better understanding of the present invention, including the various objects and advantages thereof, reference is made to the following description, which is to be taken in conjunction with the accompanying illustrative drawings.

FIGS. 11a-d show perspective and cross-sectional views of how the same protector can accommodate cannulae or sensors of various lengths, according to some embodiments of the present invention.

FIGS. 17a-c show exemplary pen-like inserter and cannula cartridge unit, according to some embodiments of the present invention.

FIGS. 18a-f are cross-sectional views of an exemplary cannula insertion process where the pen-like inserter, shown in FIG. 17a is employed, according to some embodiments of the present invention.

FIG. 19h is a cross-sectional view of the inserter shown in FIG. 19a.

DETAILED DESCRIPTION OF THE INVENTION

Figure 1A:
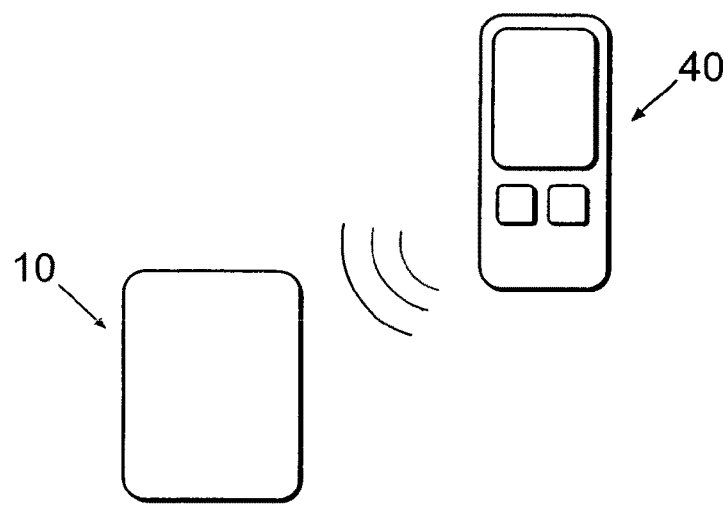
FIGS. 1a-c show exemplary single-part dispensing unit, two-part dispensing unit and remote control unit, according to some embodiments of the present invention.

A skin adherable insulin delivery device was disclosed in the co-owned, co-pending International Patent Application No. PCT/IL07/000932, entitled "Systems, Devices, and Methods for Fluid/Drug Delivery", filed Jul. 24, 2007, claiming priority to U.S. Provisional Patent Application Nos. 60/833,110, filed Jul. 24, 2006, and 60/837,877, filed Aug. 14, 2006, and further disclosed in the co-owned, co-pending U.S. patent application Ser. No. 12/004,837, and International Patent Application No. PCT/IL07/001578, both filed Dec. 20, 2007 and entitled "Systems, Devices, and Methods for Sustained Delivery of a Therapeutic Fluid", and claiming priority to U.S. Provisional Patent Application No. 60/876,679, filed Dec. 22, 2006, the disclosures of which are incorporated herein by reference in their entireties. The devices in these applications include a remote control unit and a skin adherable unit ("dispensing patch unit"). The dispensing patch unit can be coupled with a unique cannula apparatus, which does not require an infusion set and long tubing. The cannula apparatus allows the patient to choose the desired depth of penetration and angle for cannula insertion. In one embodiment the dispensing patch unit is provided with a "well assembly" connected to an inner insulin delivery tube. The well assembly has an upper opening and a lower rubber gasket. An insertion apparatus is provided with a "penetrating cartridge" comprising a cannula, penetrating member and rubber cap. The penetrating cartridge allows for the cannula to penetrate through the well assembly and then through the skin, while the upper opening remains sealed and delivery of insulin is maintained.

In another embodiment of the device it is provided with a "cradle unit". The cradle unit is configured as a sheet with an adhesive layer that is attached to the skin before cannula insertion, and it is used to allow connection and disconnection of the dispensing patch unit to and from the body. The cannula is inserted through the cradle unit into the skin and remains rigidly connected to the cradle unit after insertion. The penetrating member (metallic sharp needle) is then retracted and disposed of.

In another co-owned/co-pending U.S. Provisional Application No. 60/937,214, filed on Jun. 25, 2007 and entitled "Insertion Device for Inserting a Cannula into a Body", a device ("inserter") and a method for automatic insertion of a cannula associated to a skin adherable dispensing device are disclosed. The inserter is preloaded with a cradle unit and a "cannula cartridge unit", including a cannula, a penetrating member and a protector. The cannula cartridge unit will be discussed further in connection with the present invention. The user attaches the cradle unit to the skin and consecutively fires the cannula through the cradle unit into the body. The penetrating member is then retracted manually or automatically and disposed of.

Continuous glucose monitors are disclosed the co-owned, co-pending International Patent Application No. PCT/IL07/001096, filed Sep. 5, 2007, entitled "Fluid Delivery System With Optical Sensing of Analyte Concentration Levels", and claiming priority to U.S. Provisional Patent Applications No. 60/842,869, filed Sep. 6, 2006, and International Patent Application No. PCT/IL007/001177, filed Sep. 25, 2007, entitled "Fluid Delivery System with Electrochemical Sensing of Analyte Concentration Levels", and claiming priority to U.S. Provisional Patent Application No. 60/848,511, filed Sep. 29, 2006.

The further description of the invention deals mostly with insertion of a cannula. It should be borne in mind however that this description may be equally used for insertion of a sensor for sensing bodily analyte or for insertion of any other subcutaneously insertable element.

Figure 1B:
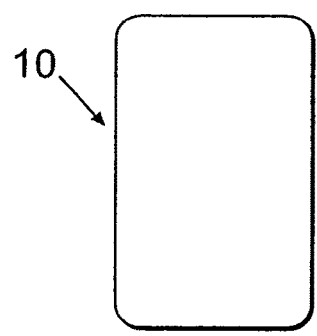
Figure 1C:
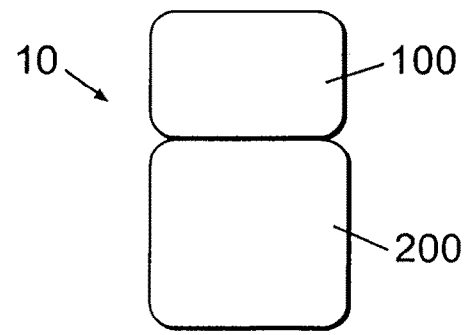

FIG. 1a shows an exemplary fluid delivery device having a dispensing unit or a dispensing patch unit (10) for dispensing therapeutic fluid to the body of a user and a remote control unit (40) for remotely controlling operation of the unit (10). Such remote control can include sending and receiving instructions to and from the dispensing unit (10) via wireless, wired, RF, or any other methods of communication. The remote control unit (40) can be a mobile telephone, a PDA, a laptop computer, an iPod, a personal computer, a remote control device, or any other suitable device. Throughout the following description, the terms dispensing unit and dispensing patch unit will be used interchangeably. The dispensing patch unit (10) may be composed of a single part (as shown in FIG. 1b) or two parts (as shown in FIG. 1c), e.g., a reusable part (100) and a disposable part (200). The reusable part (100) and the disposable part (200) are connected to each other to make the dispensing unit operational, i.e., capable of dispensing fluid to the user. In some embodiments, the fluid is insulin.

Figure 2A:
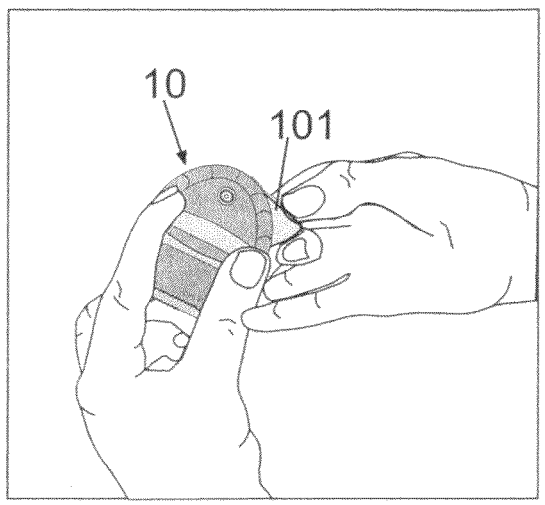
FIGS. 2a-c show an exemplary dispensing unit directly adhered to the skin of a user, according to some embodiments of the present invention.
Figure 2B:
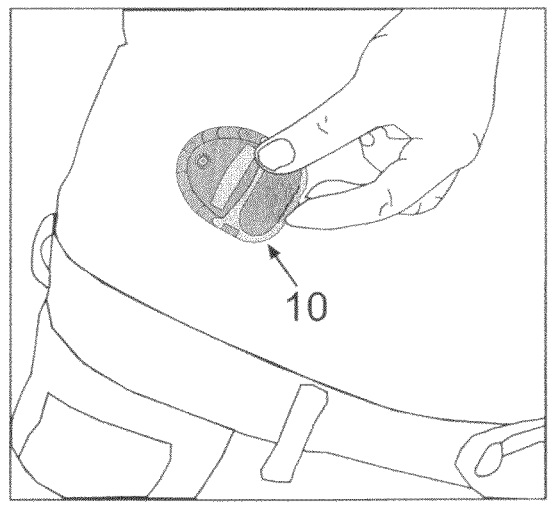
Figure 2C:
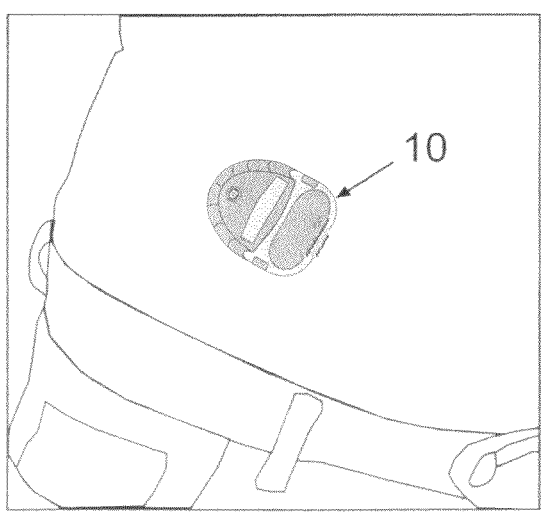

FIGS. 2a-c illustrate exemplary adherence of a dispensing patch unit (10) to the skin (5) of the patient. FIG. 2a shows peeling of an adhesive protective sheet (101) from the dispensing patch unit (10). FIG. 2b shows adherence of the dispensing patch unit (10) to the skin (5) of the patient. FIG. 2c shows the dispensing patch unit (10) adhered to the skin (5) and being ready for operation.

Figure 3A:
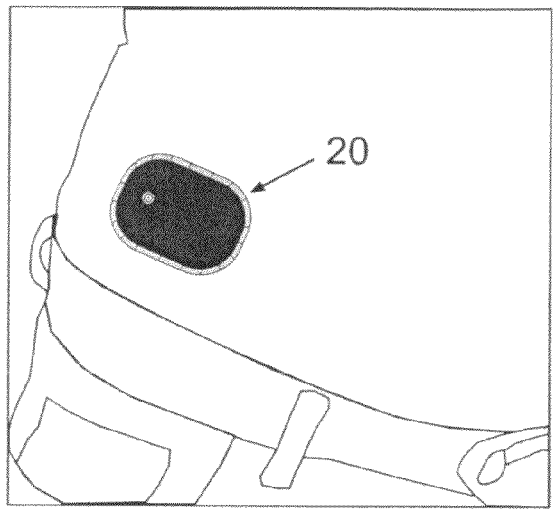
FIGS. 3a-c show an exemplary connection of the dispensing unit to a cradle unit, according to some embodiments of the present invention.
Figure 3B:
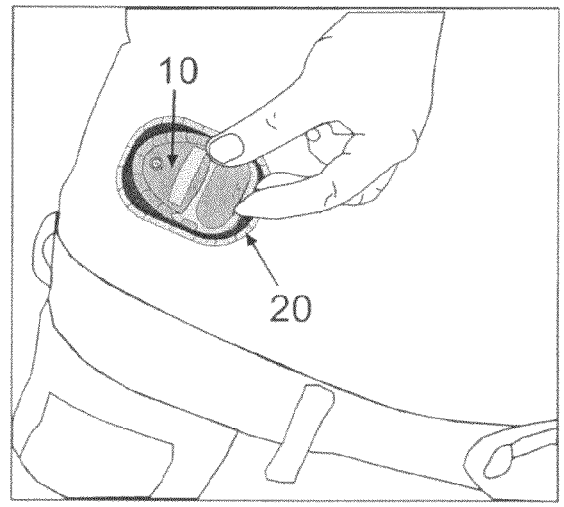
Figure 3C:
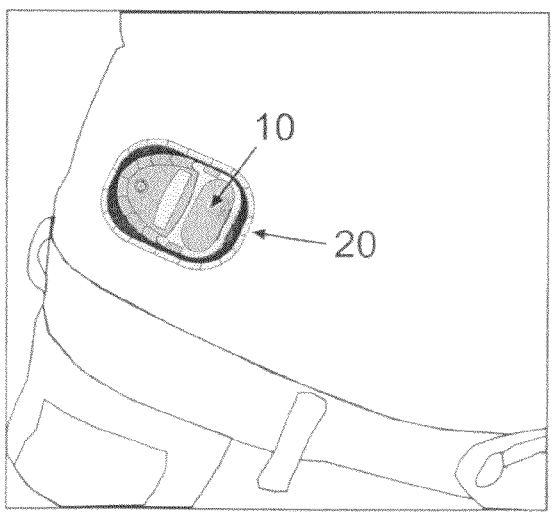

In some embodiments, as illustrated in FIGS. 3a-c, the present invention's device can implement a cradle unit (20), which can be initially adhered to the skin (5) and then the dispensing patch unit (10) can be connected to and disconnected from the cradle unit (20) upon patient's discretion. The device employing the cradle unit is described in the co-owned, co-pending International Patent Application No. PCT/IL07/001578, filed Dec. 20, 2007 and entitled "Systems, Devices, and Methods for Sustained Delivery of a Therapeutic Fluid", and claiming priority to U.S. Provisional Patent Application No. 60/876,679, filed Dec. 22, 2006, the disclosures of which are incorporated herein by reference in their entireties.

FIG. 3a shows the cradle unit (20) being adhered to the skin (5). FIG. 3b shows connection of the dispensing patch unit (10) to the adhered cradle unit (20). FIG. 3c shows the dispensing patch unit (10) being connected to the cradle unit (20) and ready for operation.

Figure 4A:
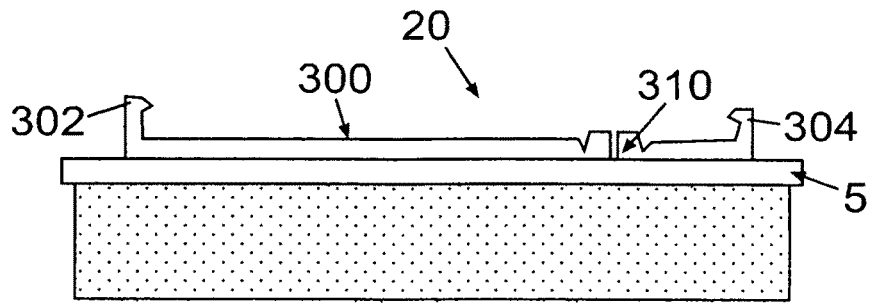
FIGS. 4a-b show schematically an exemplary cradle unit, according to some embodiments of the present invention.
Figure 4B:
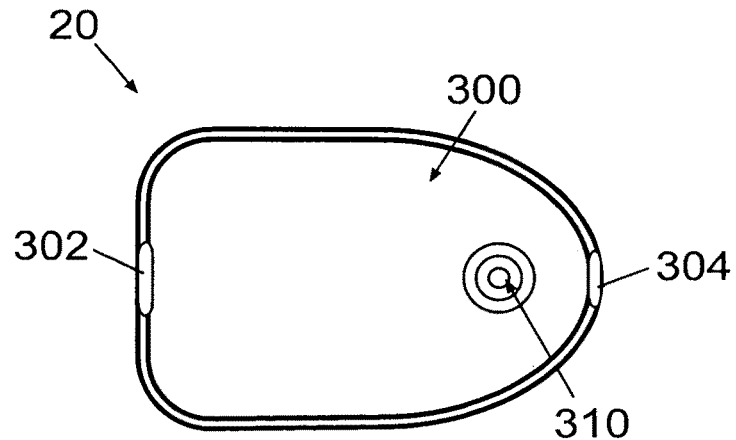

FIGS. 4a-b show side and upper views, respectively, of the cradle unit (20). In some embodiments, the cradle unit (20) can include the following components:

A cradle base (300) that can be configured as a flat sheet with an adhesive layer facing the skin (5) and with anchoring means (302), (304) on its upper side for connecting and disconnecting of an inserter and the dispensing patch unit (10). FIGS. 4a-b do not show the inserter and the dispensing patch unit.

A well (310) that can be configured as a tubular protrusion emerging upwardly from the cradle base (300) to allow alignment and appropriate connection of the cradle unit (20) and the inserter (not shown), as well as, the cradle unit (20) and the dispensing patch unit (10). In some embodiments, the well constitutes a tubular passage through which fluid is delivered by the dispensing patch unit to the body.

Figure 4C:
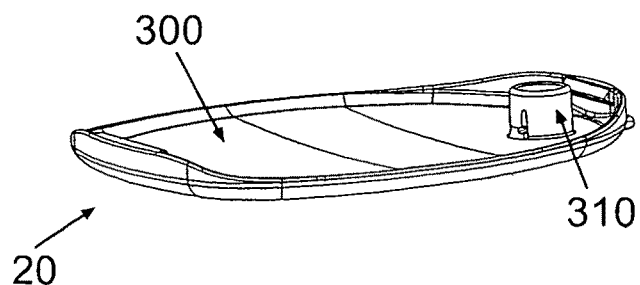
FIG. 4c shows another exemplary cradle unit, according to some embodiments of the present invention.

FIG. 4c illustrates the cradle unit (20) having cradle base (300) and well (310).

Figure 5A:
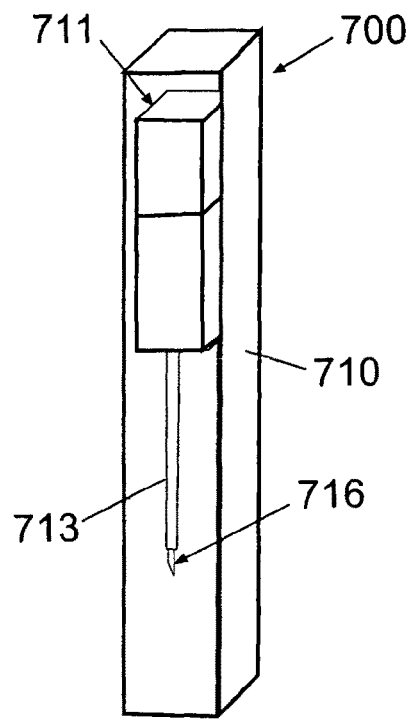
FIGS. 5a-b show schematically an exemplary cannula cartridge unit as a stand-alone item and after it has been loaded into an inserter, according to some embodiments of the present invention.

FIG. 5a shows schematically an exemplary cannula cartridge unit (700), according to some embodiments of the present invention. The cannula cartridge unit (700) includes a protector (710) and a penetrating cartridge (711). The penetrating cartridge (711) includes a cannula (713) that is used for maintaining fluid (e.g., insulin) delivery from the dispensing patch unit (10) to the body of the patient and/or for analyte (e.g., glucose) sensing. The penetrating cartridge (711) also includes a penetrating member (716) that pierces the skin (5) and facilitates insertion of the cannula (713). The protector (710) is configured as a protective cover that conceals and guards the cannula (713) and the penetrating member (716). Thus, the user is protected from unintentional skin piercing. As can be understood by one having ordinary skill in the art, the shape and size of the protector (710) are not limited to the specific shape and size shown in FIG. 5a, and it can also be designed to contain multiple cannulae.

Figure 5B:
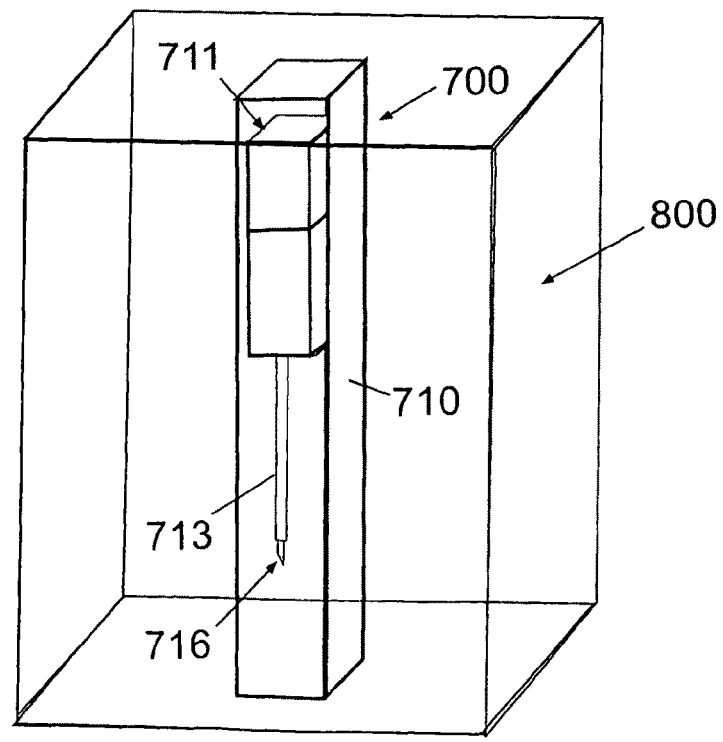

The cannula cartridge unit (700) is configured as a modular piece that can be loaded into an inserter (800), as shown in FIG. 5b. The inserter (800) allows either automatic or manual advancement of the cannula (713) and the penetrating member (716) from the protector (710) and into the body of the user (e.g., during a hypodermic cannula insertion), as will be discussed in detail below. After insertion, the cannula (713) remains in the body of the user and the penetrating member (716) is retracted back into the protector (710). The process concludes with the unloading of the protector (710) (with the penetrating member (716) disposed inside) from the inserter (800) and disposal of the item.

The cannula cartridge unit (either as a stand-alone item, in which case the insertion can be manual, or after it has been loaded into an inserter) can be used in conjunction with the cradle unit, or in conjunction with any skin adherable dispensing patch unit, which delivers the fluid using a well assembly or an infusion set, or in conjunction with a non-adherable dispensing unit (e.g., a pager-like pump), which delivers the fluid using an infusion set. Exemplary dispensing patch units having a well assembly were disclosed in detail in co-pending, co-owned International Patent Application No. PCT/IL07/000932, entitled "Systems, Devices, and Methods for Fluid/Drug Delivery", filed Jul. 24, 2007, claiming priority to U.S. Provisional Patent Application Nos. 60/833,110, filed Jul. 24, 2006, and 60/837,877, filed Aug. 14, 2006, the disclosures of which are incorporated herein by reference in their entireties.

Figure 6A:
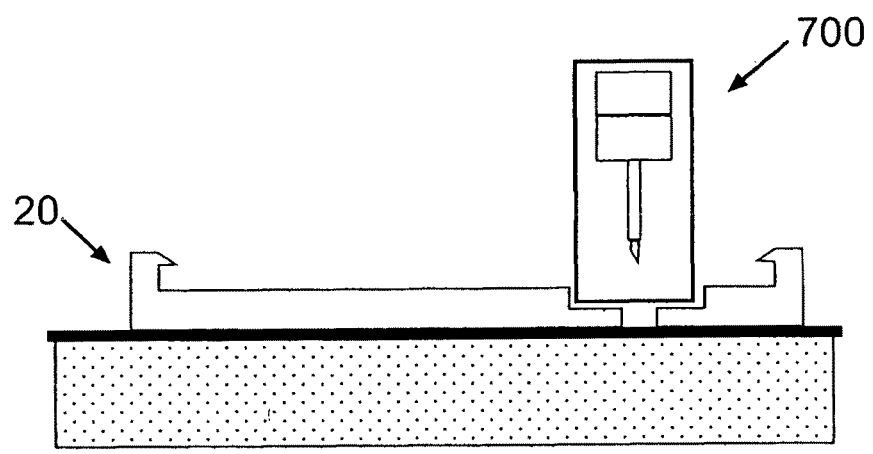
FIGS. 6a-c show the cannula cartridge unit connected to an exemplary cradle unit (FIG. 6a), an exemplary well assembly (FIG. 6b), and an exemplary infusion set (FIG. 6c), according to some embodiments of the present invention.
Figure 6B:
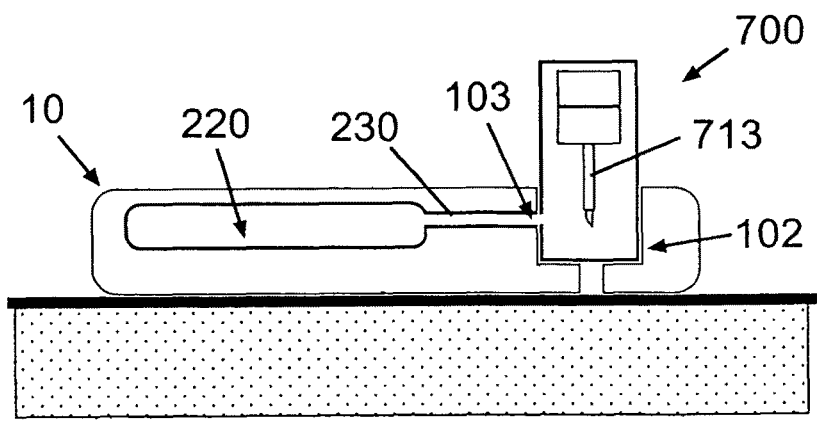
Figure 6C:
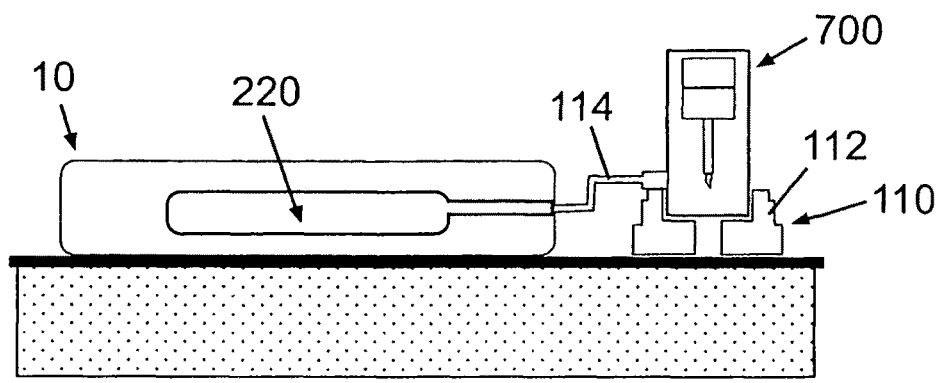

FIG. 6a shows the cannula cartridge unit (700) connected to the cradle unit (20). After the cannula insertion process is completed, the cannula cartridge unit (700) is disconnected from the cradle unit (20) and the dispensing patch unit is connected to the cradle unit (20), as will be described below. FIG. 6b shows the cannula cartridge unit (700) connected to a well assembly (102), which can be employed in a single-part dispensing patch unit (10) or in a two-part dispensing patch unit. The well assembly (102) has an inlet port (103) on its side to allow the passage of dispensed fluid from a reservoir (220) via a delivery tube (230) to the cannula (713), through a lateral opening (not shown in FIG. 6b) made in the cannula (713). FIG. 6c shows an embodiment, where the cannula cartridge unit (700) is connected to an infusion set (110) disposed outside the dispensing unit (10). In this embodiment, the dispensing unit (10) can be adherable to the skin of the patient, as illustrated in FIG. 6c, or non-adherable thereto, e.g., it can be configured as a pager-like pump. The infusion set (110) includes a hub (112) and a short connecting tube (114) for connecting the dispensing patch unit (10) to a proximate insertion site. The connecting tube (114) is in fluid communication with a reservoir (220).

Figure 7A:
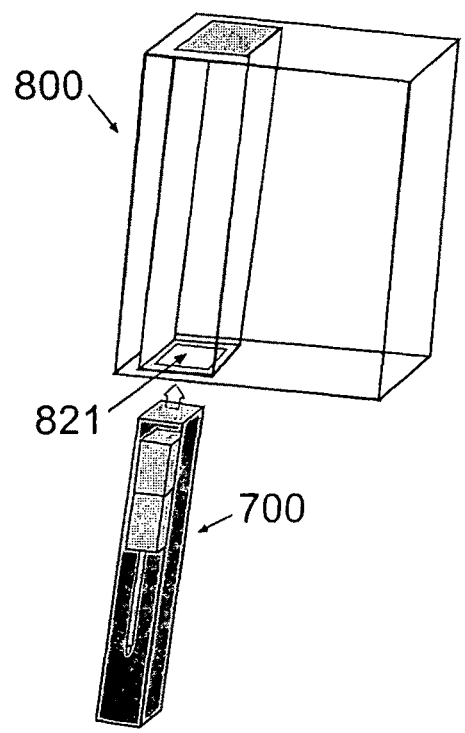
FIGS. 7a-c show exemplary loading of the cannula cartridge unit into an inserter, according to some embodiments of the present invention.
Figure 7B:
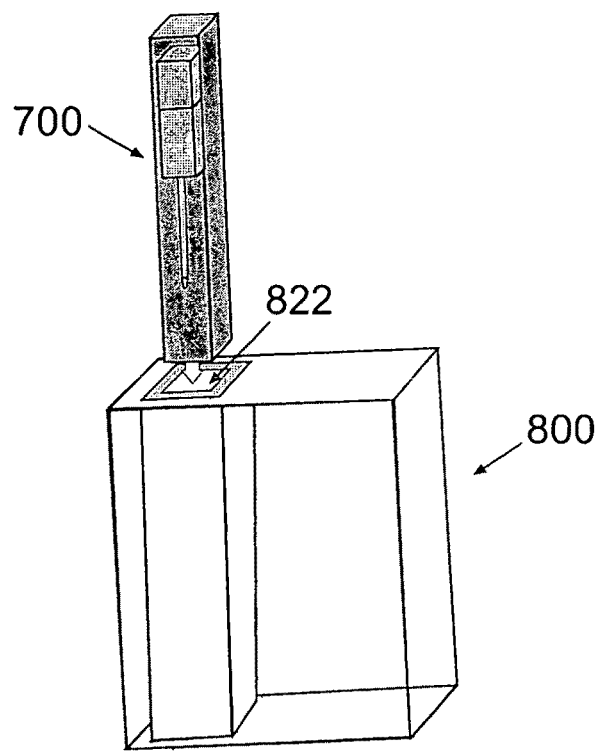
Figure 7C:
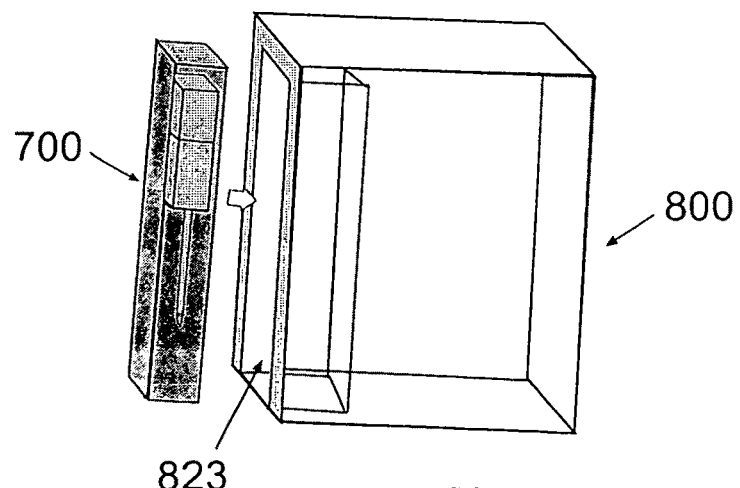

FIGS. 7a-c show various ways of loading the cannula cartridge unit (700) into an inserter (800), according to some embodiments of the present invention. The cannula cartridge unit (700) can be loaded into the inserter (800) through a bottom opening (821) (FIG. 7a), upper opening (822) (FIG. 7b), or lateral opening (823) (FIG. 7c).

Figure 8A:
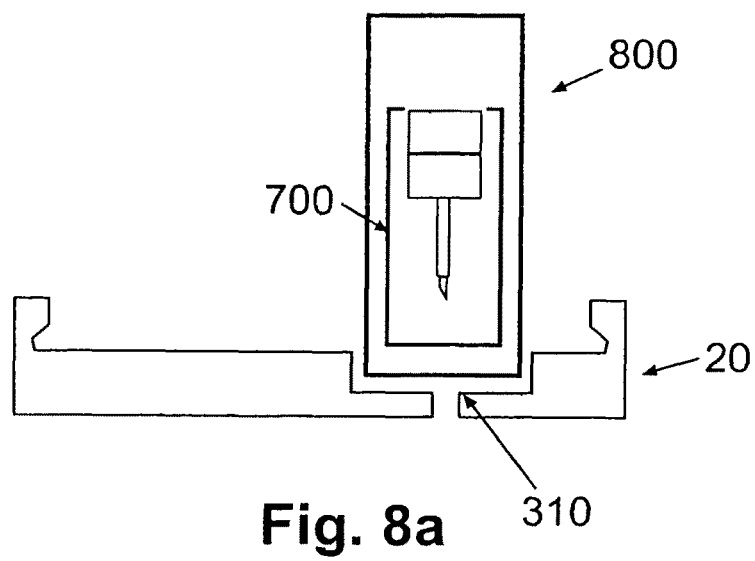
FIGS. 8a-b shows an exemplary cannula cartridge unit loaded into various types of inserters, according to some embodiments of the present invention.
Figure 8B:
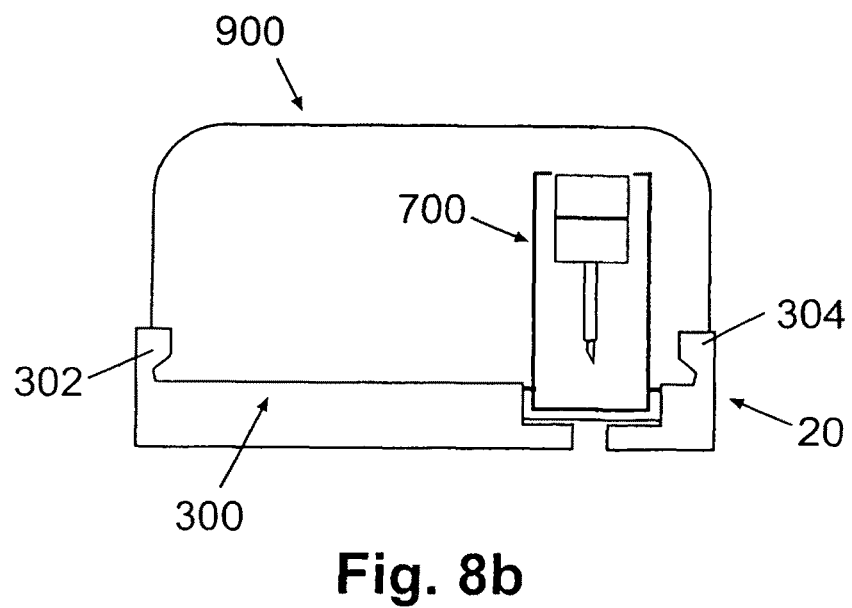

The cannula cartridge unit (700) can be designed as a modular piece that can be loaded into various types of inserters. FIG. 8a schematically shows the inserter being configured in a form of a pen (800). The pen (800) can be connected to the cradle unit (20) via the well (310). FIG. 8b schematically shows the inserter being configured in form of a dome-shaped unit, e.g., a computer mouse (hereinafter referred to as "mouse-like"), (900), which can be connected to the cradle unit (20) using anchoring means (302), (304) provided on an upper side of the cradle base (300). As can be understood by one skilled in the art, these examples are provided here for illustrative purposes and are not intended to limit the present invention. The present invention can employ various types of inserters, into which the cannula cartridge unit can be loaded.

Figure 9A:
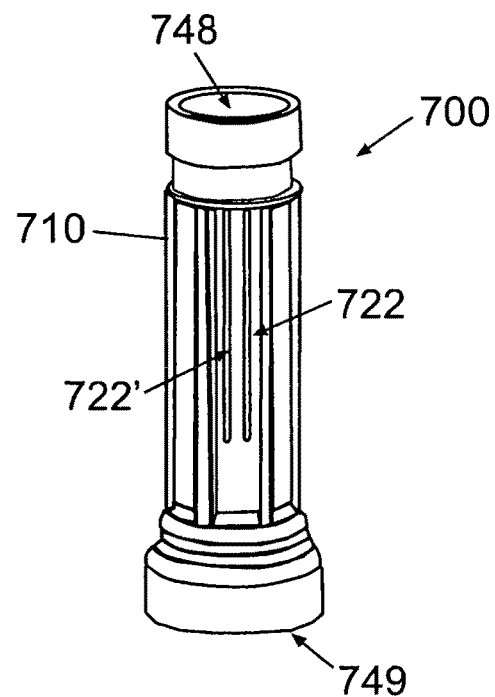
FIGS. 9a-b show perspective and cross-sectional views of an exemplary cannula cartridge unit, according to some embodiments of the present invention.

FIG. 9a is a perspective view of the exemplary cannula cartridge unit (700), having the protector (710) covering the cannula and the penetrating member (not shown in FIG. 9a). The protector (710) includes an upper end (748) and a bottom end (749). The protector (710) further includes at least one longitudinal slit (722), (722') disposed between the upper end (748) and the bottom end (749). The upper end (748) and the bottom end (749) are both open and are configured to allow protraction of the penetrating cartridge (not shown in FIG. 9a) from the protector (710) towards the body of the patient and retraction of the penetrating member back into the protector (710). The bottom end (749) is open and is configured to be coupled to the well assembly of the dispensing unit or to the infusion set hub, or to the well which is part of the cradle unit. In some embodiments, the bottom end (749) of the protector (710) can be designed to precisely fit over the well assembly (i.e., the size of the bottom end can be configured to accommodate the size of the well assembly), or of the infusion set hub, or of the well which is part of the cradle unit. Cannula insertion is carried out by thrusting the penetrating cartridge, manually or automatically using dedicated means. Such dedicated means can be either a rod that pushes the penetrating cartridge down through the upper end (748), or at least one hook that forcibly displaces the penetrating cartridge through at least one longitudinal slit (722), (722') disposed in the wall of the protector (710), as will be discussed below. The hook is configured to access the penetrating cartridge through the slit and is not limited to any specific shape, material or design.

Figure 9B:
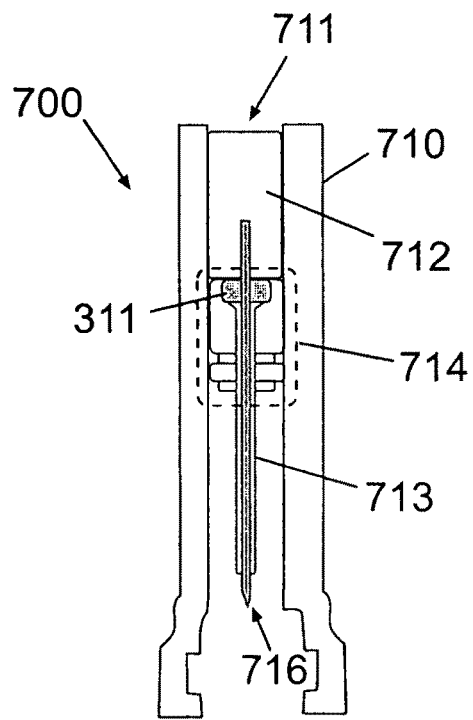

FIG. 9b is a cross-sectional view of the exemplary cannula cartridge unit (700) shown in FIG. 9a and having the protector (710) and the penetrating cartridge (711). In some embodiments, the penetrating cartridge (711) includes the following components: the penetrating member (716) having a grip portion (712) located at the blunt end of the penetrating member (716), and the cannula (713). Additionally, the penetrating cartridge can include a cannula hub (714), which is attached to the cannula (713) and contains a self-sealable septum (311) for sealing the cannula (713) after it has been inserted through the well into the body of the user. The septum (311) can be pierced repeatedly by a connecting lumen provided in the disposable part of the dispensing patch unit, as will be described below, for maintaining fluid communication between the reservoir and the cannula (713).

Figure 10:
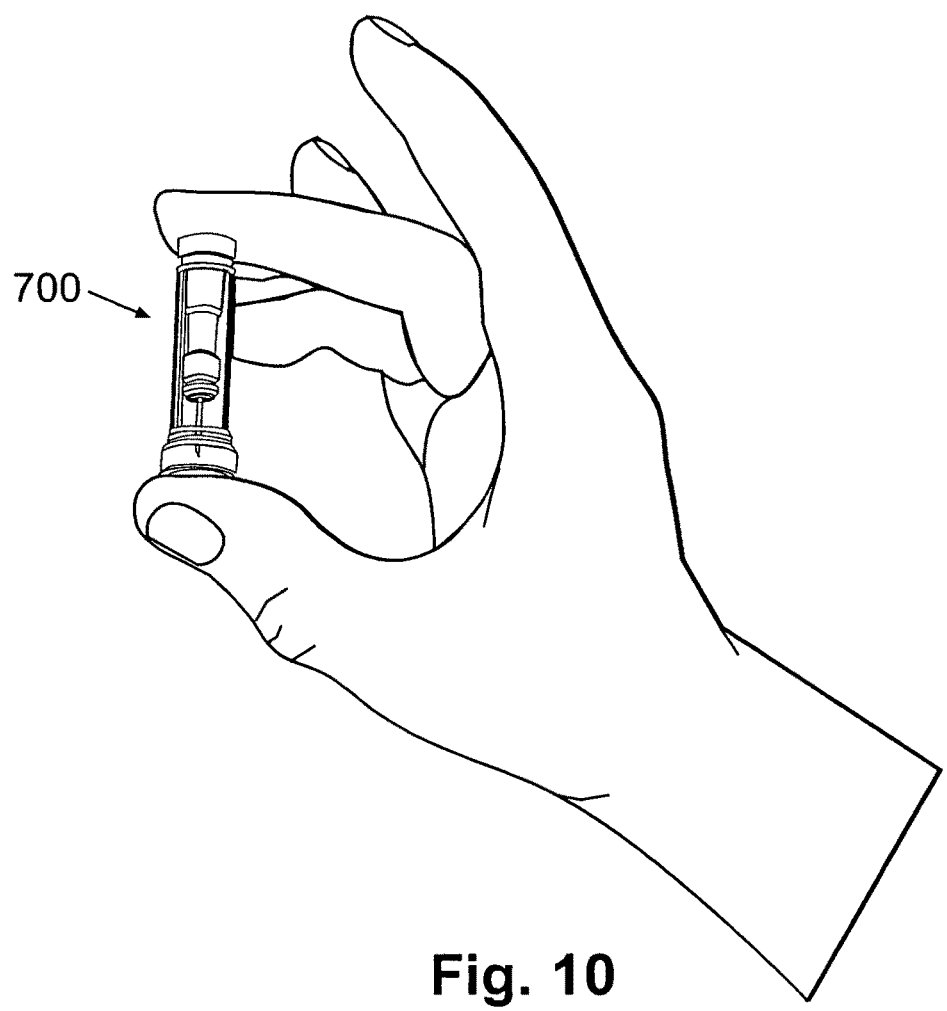
FIG. 10 shows a user's hand holding the cannula cartridge unit, according to some embodiments of the present invention.

In some embodiments, the cannula cartridge unit equipped with a dedicated protector has the following advantages. One of the advantages is that the user is protected from unintentional skin piercing, as for example illustrated in FIG. 10. Moreover, since the user does not see the penetrating member, as it is concealed within the protector before and after insertion, the dedicated protector provides an important psychological advantage over conventional insertion devices, where the user is able to see the needle, which may cause some users to have an adverse reaction. Additionally, the protector prevents direct contact by the user with the cannula (e.g., touching the cannula with user's hands), thereby maintaining sterility of the cannula. Further, a single protector (having pre-defined dimensions) can accommodate variably sized/shaped cannulae and/or sensors having various sizes/shapes. This is advantageous since differently sized/shaped cannulae may be inserted at different insertion sites, where user may have different fat layer thicknesses. Thus, a single inserter can be loaded with a single dedicated cannula cartridge unit that is tailored specifically to patient requirements. In some embodiments, the protector can accommodate insertion of a subcutaneously insertable element that can include a cannula, a probe, and/or a sensor. The subcutaneously insertable element can be used for both fluid delivery and analyte sensing as well as other tasks.

FIGS. 11a-d are perspective and cross-sectional views of the protector (710) accommodating different size cannulae and sensors. FIGS. 11a-d illustrate an exemplary 30 mm protector (710). FIGS. 11a-b show perspective and cross-sectional views of the protector (710) containing a 6 mm cannula (713). FIGS. 11c-d show perspective and cross-sectional views of the same protector (710) containing a 9 mm cannula (713). The length of the cannula (713) is not limited to the indicated lengths.

Figure 12A:
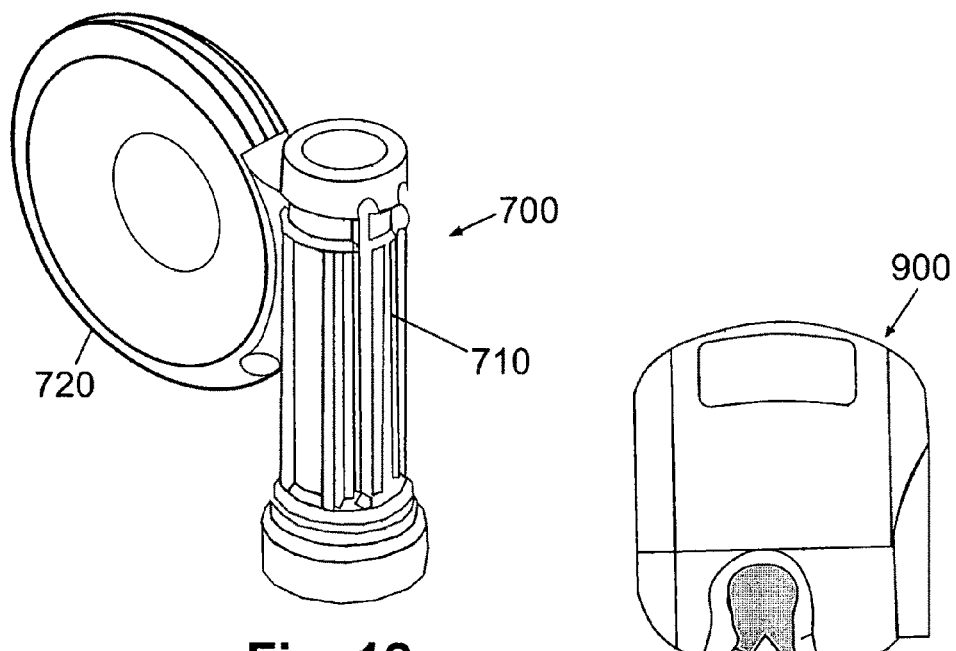
FIGS. 12a-b show an exemplary cannula cartridge unit provided with a handle and being loaded into an inserter, according to some embodiments of the present invention.
Figure 12B:
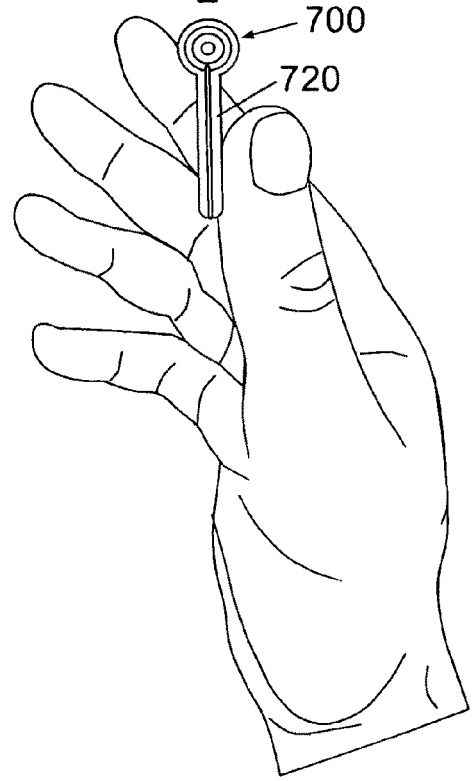

In some embodiments, the protector (710) can be provided with a handle (720), as shown in FIG. 12a (which is a perspective view of the protector with the handle), to enable convenient gripping and proper loading of the cannula cartridge unit (700) into the inserter (800), as shown in FIG. 12b (which is a top view of the protector with the handle being loaded into the dispensing unit). The handle (720) can be round, square, rectangular, or of any other desired shape and size.

Figure 13:
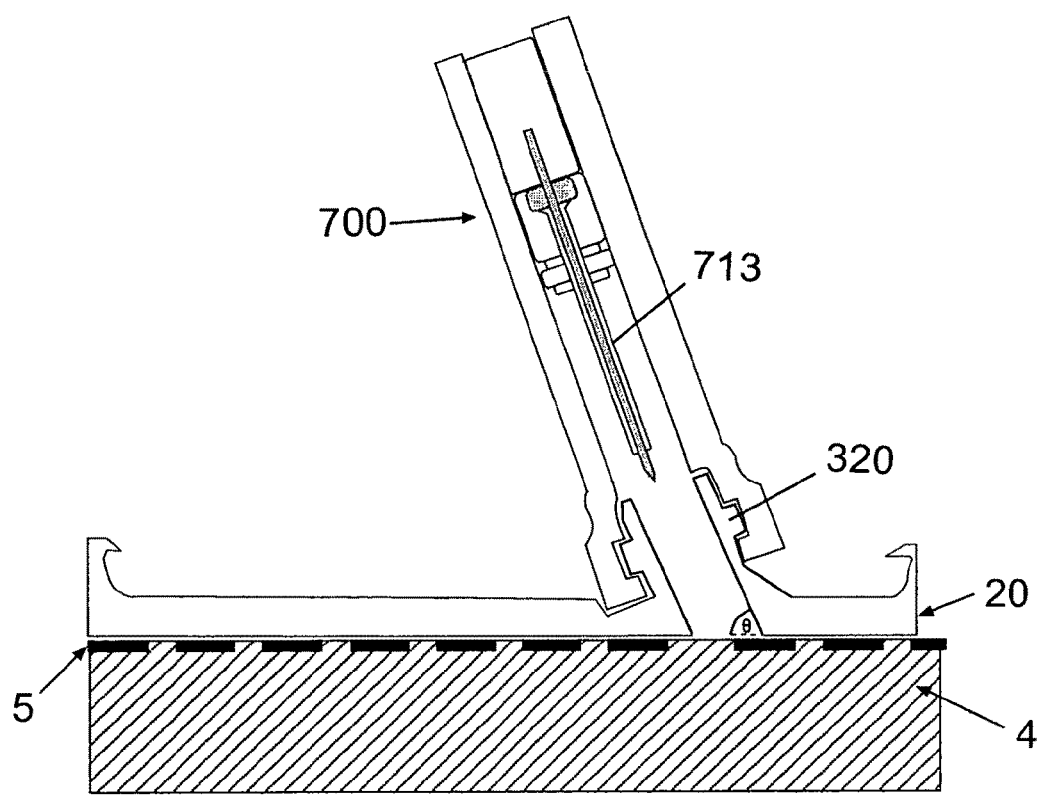
FIG. 13 shows an exemplary cannula cartridge unit connected to a tilted well, according to some embodiments of the present invention.

One of the other advantages of the protector is that, in some embodiments, the cannula cartridge unit (700) facilitates insertion of a cannula (713) at various angles, for example, by connection to a tiltable well (320), as shown in FIG. 13. The well (320) can be disposed with regard to the skin (5) of the user at an angle θ, thereby allowing insertion of the cannula (713) at an angle θ into the subcutaneous compartment (4), which can be useful when inserting the cannula at specific insertion sites. The angle θ can vary as desired by the user and/or dispensing unit design. In some embodiments, the cradle unit (20) can be designed to accommodate angular insertion of the cannula (713).

In some embodiments, the cannula insertion process, using a cannula cartridge unit, can be carried out either manual (i.e., the cannula insertion and the penetrating member retraction are performed manually), or semi-automatic (i.e., the cannula insertion can be automatic, while the penetrating member retraction can be manual and vice versa), or fully automatic (i.e., both the cannula insertion and the penetrating member retraction are automatic), as discussed in detail below.

The penetrating member and the protector can be disposable. Thus, after the cannula insertion process is completed, the protector, containing the penetrating member, can be disposed. Since the sharp penetrating member is entirely concealed and shielded by the protector, disposal of the protector can be done into a standard garbage container instead of a dedicated bio-hazard container.

Figure 14A:
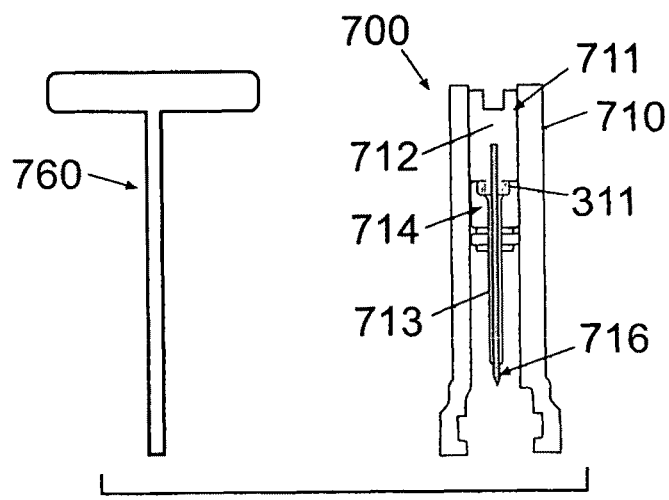
FIGS. 14a-i are cross-sectional views of an exemplary manual cannula insertion process, according to some embodiments of the present invention.
Figure 14B:
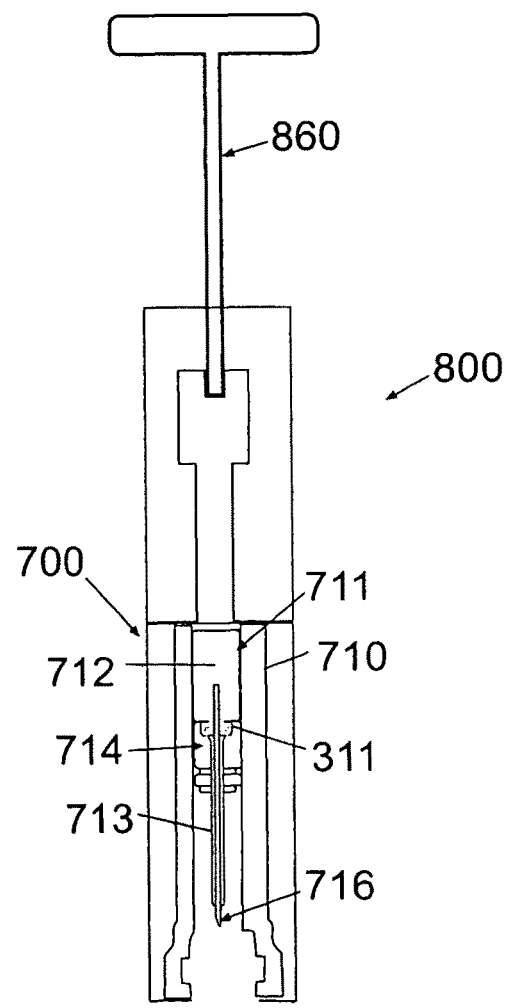

FIGS. 14a-i are cross-sectional views of the cannula cartridge unit (700) during manual insertion process. Manual insertion can be carried out using the cannula cartridge unit (700) being a stand-alone item with the aid of a dedicated rod (760) (as shown in FIG. 14a) or by loading the cannula cartridge unit (700) into the inserter (800) provided with a rod (860) (as shown in FIG. 14b). The insertion process in both embodiments is substantially similar. FIGS. 14c-i illustrate the insertion process using the cannula cartridge unit (700) as a stand-alone item together with the skin adherable cradle unit (20).

Figure 14C:
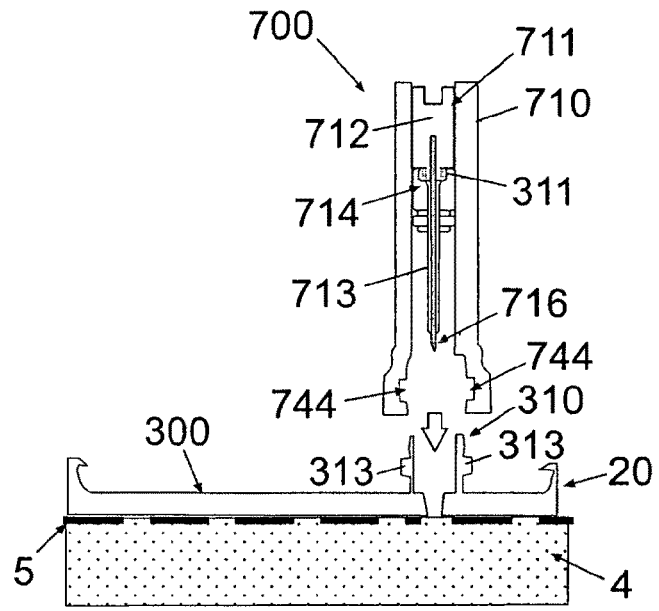
Figure 14D:
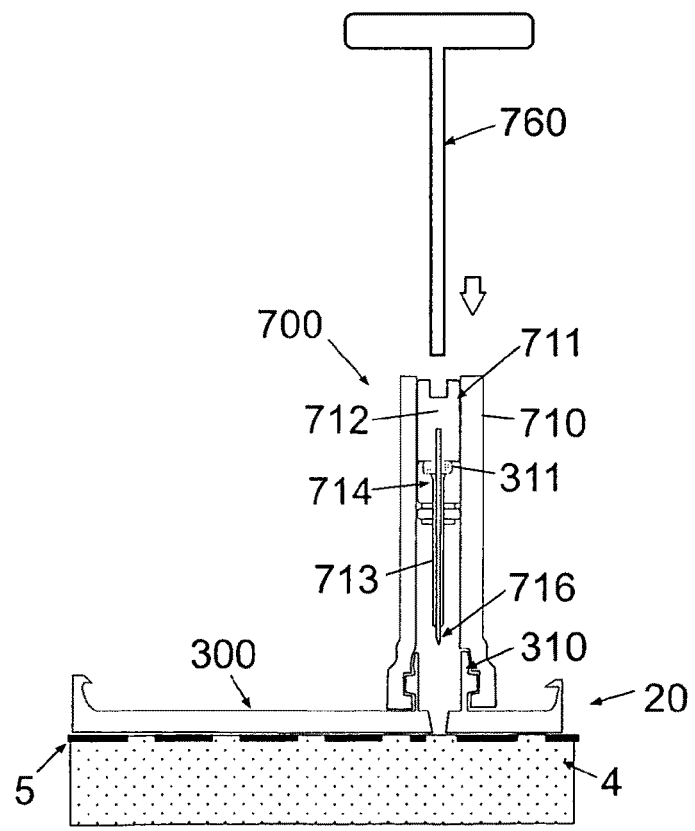

FIG. 14c shows the cannula cartridge unit (700) and the cradle unit (20) prior to being connected. The cradle unit (20) includes the well (310) disposed in the base (300) and having a snapping engagement mechanism with a resistance loaded annular latch (313). The cannula cartridge unit (700) includes an annular notch or recess (744) that corresponds and is configured to accommodate insertion of the annular latch (313). As discussed above, the cannula cartridge unit (700) is placed over the well (310), thereby snapping the notch (744) over the latch (313) and therefore locking the unit (700) to the well (310). As can be understood by one skilled in the art, other ways of securing the unit (700) to the well (310) are possible. In some embodiments, the cannula cartridge unit (700) can be only placed over a well (310) without being connected to the well (310). FIG. 14d shows the cannula cartridge unit (700) being connected to the cradle unit (20) via the well (310) and ready for operation. The dedicated rod (760) is disposed outside the open top end of the cannula cartridge unit (700).

The rod (760) includes a handle and a push rod that can be configured to be a blunt end located opposite the handle. The cannula cartridge unit (700) includes the penetrating cartridge (711) and a recessed grip portion (712) that accommodates placement of the blunt end of the rod (760). The recessed grip portion (712) secures the rod (760) and prevents wobbling of the rod (760) when the latter is being pushed down the cannula cartridge unit (700).

Figure 14E:
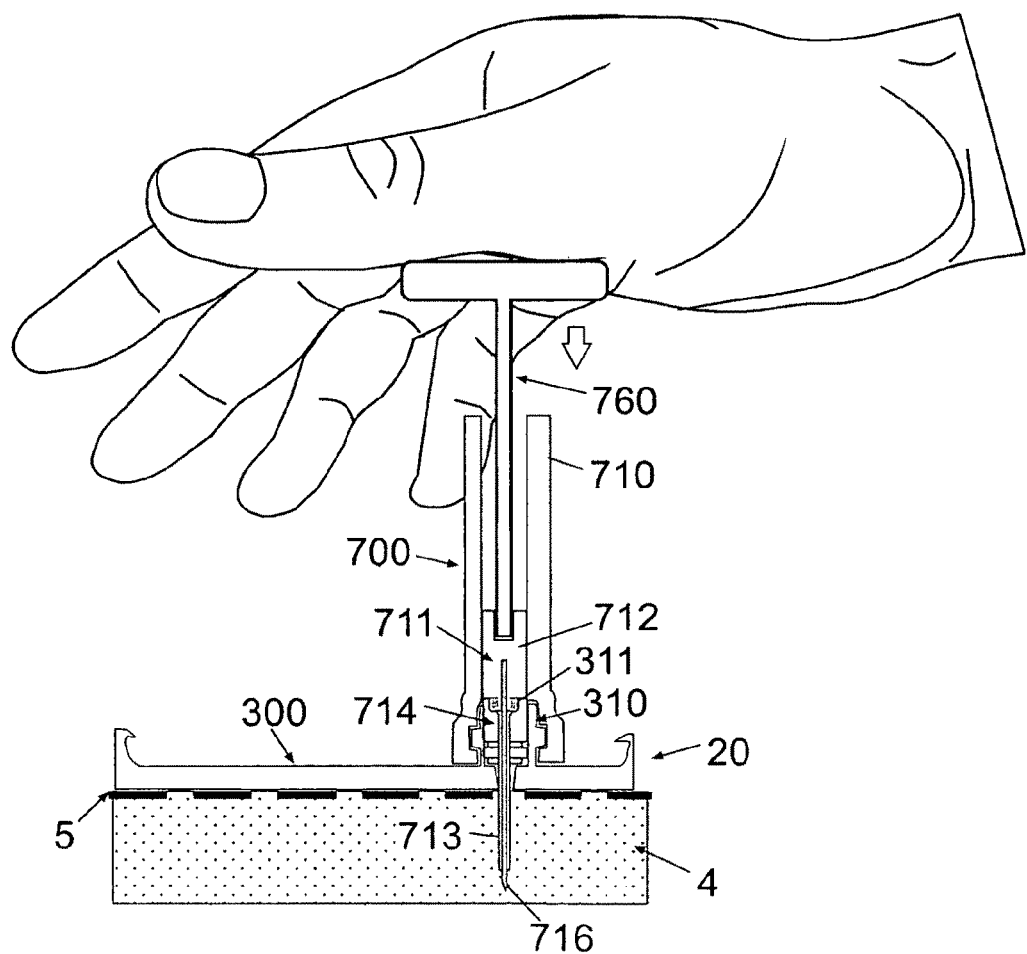

FIG. 14e shows the penetrating cartridge (711) being pushed down by the rod (760) through the well (310) and into the subcutaneous tissue (4) of the user. The user pushes on the handle of the rod (760) to thrust the rod (760) in a downward direction toward the well (310). The force that the user applies to the handle is transferred to the penetrating cartridge (711) that is being pushed down toward the skin of the user. The pushing or thrusting of the penetrating cartridge (711) can be carried out using a rod, as illustrated, or the user's finger, or any other means. As the penetrating cartridge (711) is pushed down, the penetrating member (716) pierces the skin (5) of the user and enters the subcutaneous tissue (4). Along with the entry of the penetrating member (716), the cannula (713) is also inserted into the subcutaneous compartment (4). Once the cannula (713) is inserted, the penetrating member (716) can be removed.

Figure 14F:
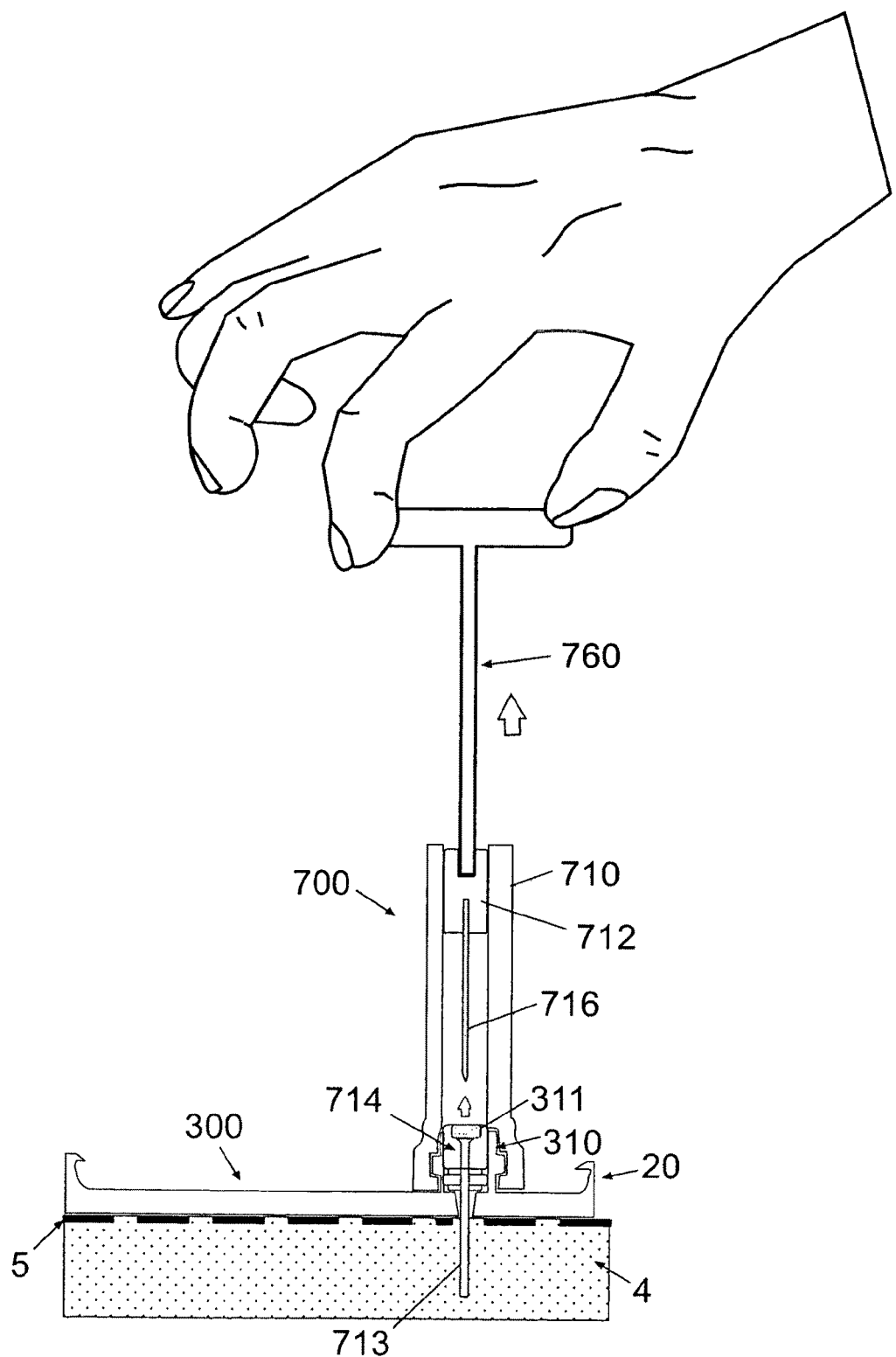

FIG. 14f shows retraction of the penetrating member (716) back into the protector (710) using the rod (760). Once the cannula (713) is inserted into the subcutaneous tissue (4), the cannula hub (714) remains rigidly connected to the well (310). To remove the penetrating member (716), the user pulls on the handle of the rod (760) in an upward direction (or direction opposite to the direction of insertion). Since the blunt end of the rod (760) is secured to the recessed grip portion (712) that is able to slide back and forth inside the protector (710), upon pulling of the rod (760), the grip portion (712) is pulled along with the rod (760), thereby removing the penetrating member (716) from the subcutaneous compartment (4) and the cannula hub (714). In some embodiments, the protector (710) can include stoppers at its top end to prevent accidental removal of the grip portion (712). Additionally, the protector's interior portion can include interior stoppers to prevent excessive insertion of the penetrating member (716) and accidental slip out of the penetrating member (716) along with the grip portion (712) from the bottom end of the protector (710) once it is disengaged from the well (310). In some embodiments, the well (310) can serve as a stopper to prevent excessive insertion of the penetrating member (716). Once the penetrating member (716) is removed, the protector (710) can be disengaged from the well (310).

Figure 14G:
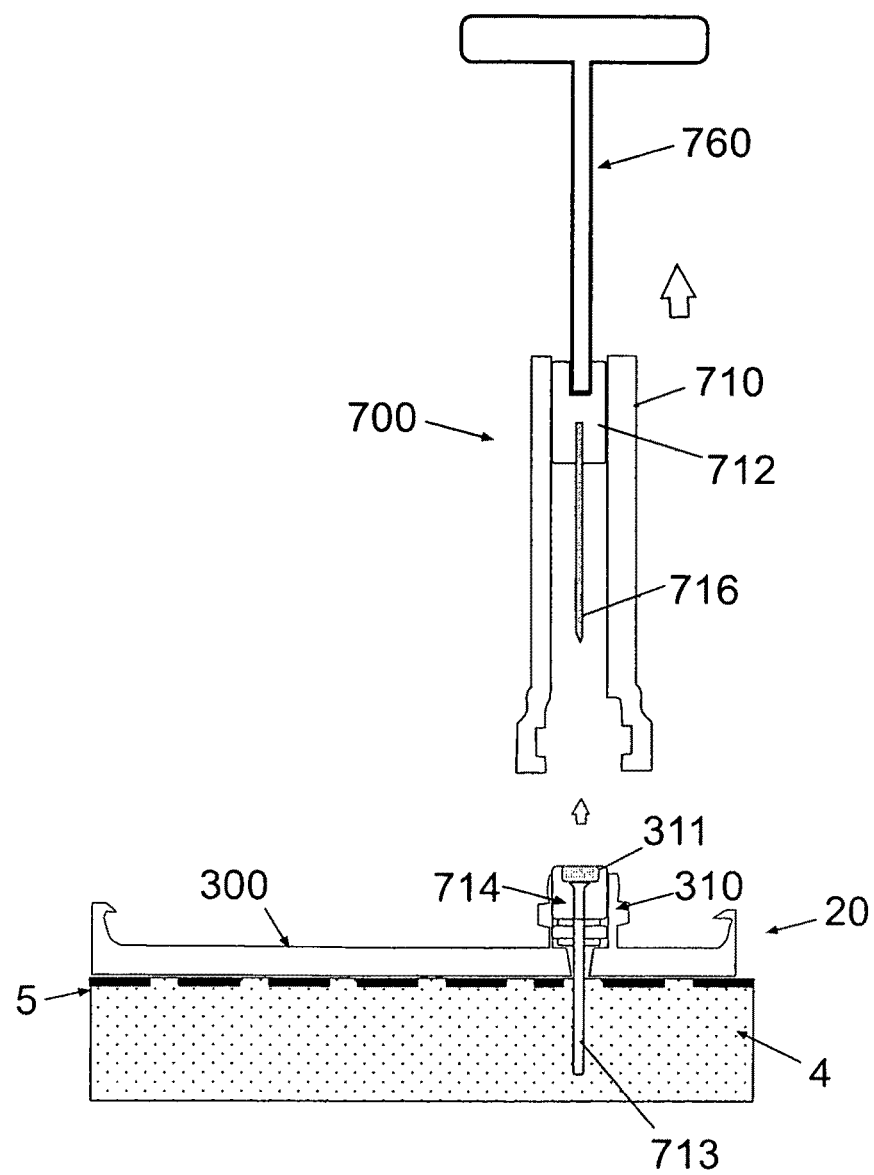

FIG. 14g shows the protector (710) being disconnected from the well (310) and the cradle unit (20). The protector (710) is removed by disengaging the notch (744) from the latch (313). This can be done by pulling the notch (744) away from the latch (313) or by pushing a button that pulls the notch (744) out, or using any other means. Upon being removed from the well (310), the protector (710) continues to conceal the penetrating member (716) along with its grip portion (712). In some embodiments, the rod (760) can be disengaged from the grip portion (712) and the protector (710) along with its contents can then be disposed. The rod (760) can be reused for future cannula insertions. In other embodiments, the rod (760) is disposable. Following retraction of the penetrating member the rod (760) can remain secured to the grip portion (712) or it can be disengaged from the grip portion (712), and the protector (710) along with its contents and the rod (760) can then be disposed. As can be understood by one skilled in the art, the protector (710) can be disconnected from the cradle unit (20) after inserting the cannula (713) while the penetrating member (716) remains inside the body. In this case, the user can manually remove the penetrating member (716) from the body by holding the grip portion (712) of the penetrating member (716) with his/her fingers and pulling it in an upward direction or a direction that is substantially opposite to the direction of insertion.

Figure 14H:
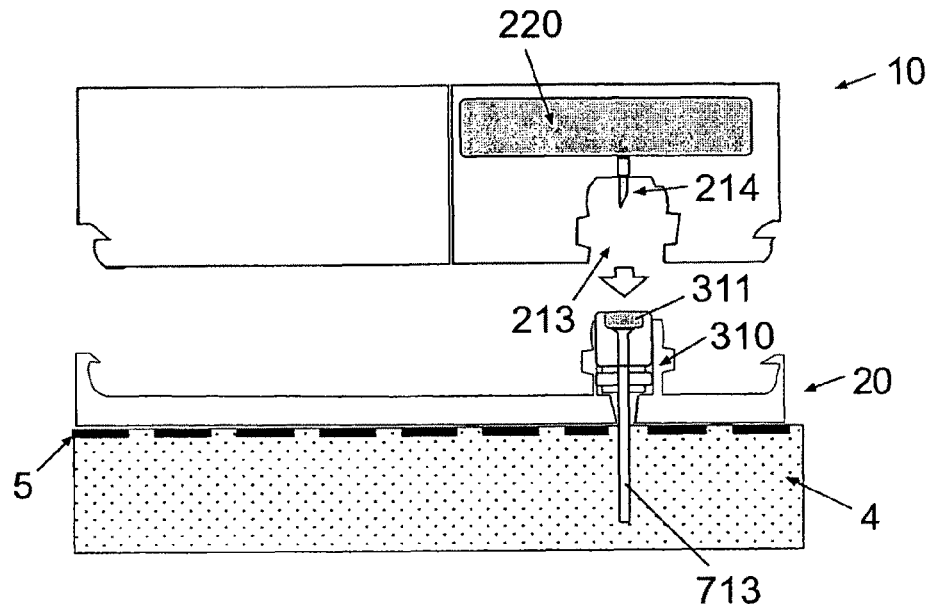

FIG. 14h shows the two-part dispensing patch unit (10) prior to being connected to the cradle unit (20). The dispensing patch unit (10) contains, inter alia, a fluid reservoir (220), an outlet port (213) and a connecting lumen (214) that maintains fluid communication between the reservoir (220) and the outlet port (213). Upon connection of the dispensing patch unit (10) and the cradle unit (20), the connecting lumen (214) pierces the septum (311) (that seals the cannula (713)), thereby allowing fluid delivery via the cannula (713) to the subcutaneous tissue (4). The outlet port (213) allows repetitive connection and disconnection of the dispensing patch unit (10) to and from the cradle unit (20).

Figure 14I:
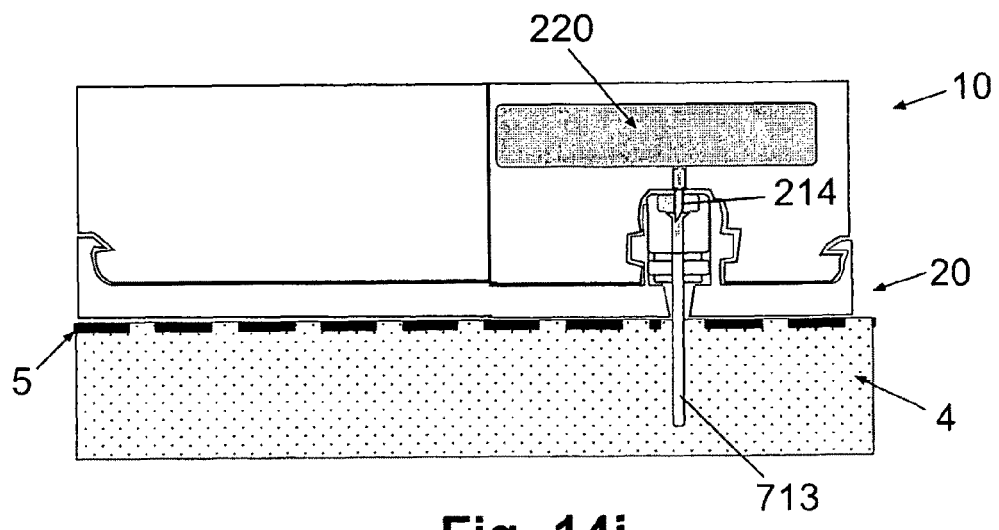

FIG. 14i shows the two-part dispensing patch unit (10) shown in FIG. 14h after it has been connected to the cradle unit (20). In some embodiments, the fluid (e.g., insulin) delivery cannula (713) can contain a sensor for monitoring a bodily analyte (e.g., glucose). Fluid delivery can be adjusted according to sensor inputs (in a semi- or fully-closed-loop system). In some embodiments, the dispending patch unit (10) includes both a cannula (713) for fluid delivery and a sensor (not shown) for analyte sensing. An example of such arrangement is disclosed in the co-owned, co-pending International Patent Application No. PCT/IL07/000163 and U.S. patent application Ser. No. 11/706,606, International Patent Application No. PCT/IL07/001579 and U.S. patent application Ser. No. 11/963,481, and in U.S. patent application Ser. No. 12/116,546 and International Patent Application No. PCT/US08/62928, filed May 7, 2008, claiming priority to U.S. Provisional Patent Application No. 60/928,054, filed May 7, 2007, and titled "A Reciprocating System for Monitoring Analyte Concentrations and/or Dispensing Fluids into a Body", the disclosures of which are incorporated herein by reference in their entireties.

Figure 15A:
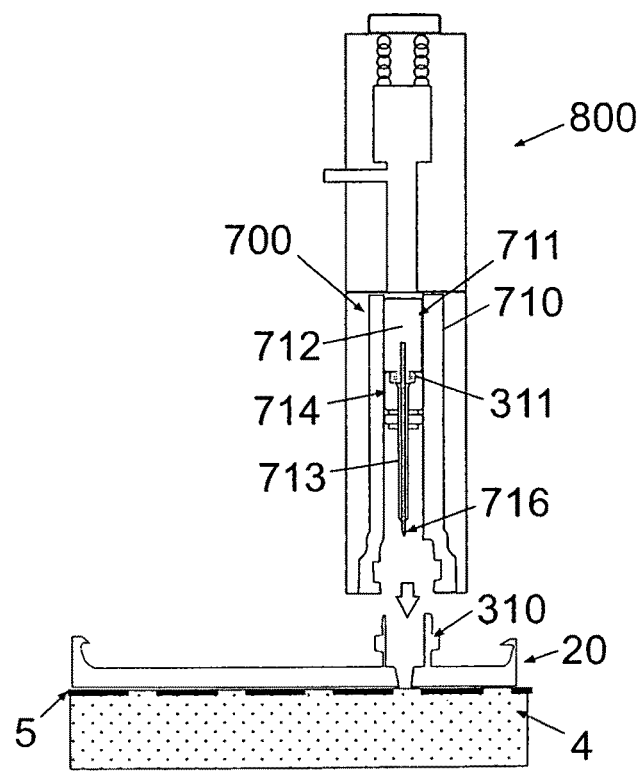
FIGS. 15a-e are cross-sectional views of an exemplary semi-automatic cannula insertion process, according to some embodiments of the present invention.

FIGS. 15a-e are a cross-sectional views of the cannula cartridge unit (700) during semi-automatic insertion process, according to some embodiments of the present invention. FIG. 15a shows the cradle unit (20) prior to being connected to the inserter (800) loaded with the cannula cartridge unit (700). The connection between the cannula cartridge unit (700) and the cradle unit (20) is established as described above with reference to FIG. 14c. In some embodiments, the inserter (800) can include a spring-loaded mechanism that is coupled to the grip portion (712) and upon release of the spring, pushes on the grip portion (712) to force insertion of the penetrating member (716) along with the cannula (713) into the subcutaneous tissue (4), as will be discussed below.

Figure 15B:
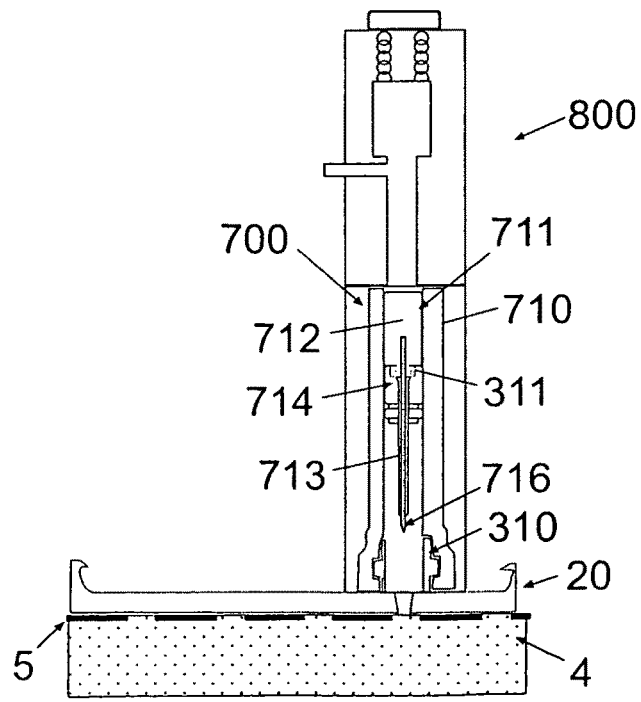

FIG. 15b shows the cannula cartridge unit (700) being connected to the cradle unit (20) and the inserter (800) being ready for operation. The inserter (800) can be connected to the well (310) in a fashion similar to the connection of the cannula cartridge unit (700) to the well (310) (e.g., using the latch-notch connection).

Figure 15C:
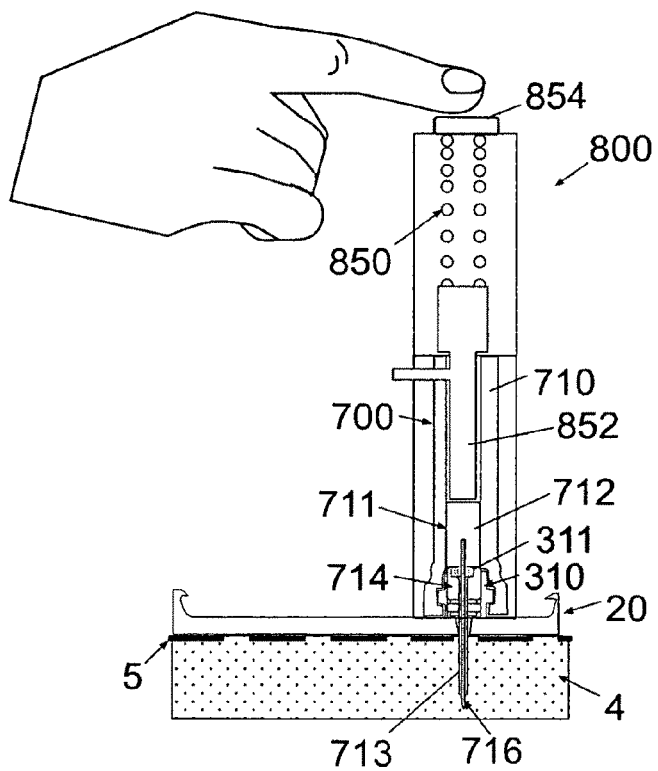

A stated above, the inserter (800) includes a spring-loaded mechanism having a spring (850) coupled to an advancing rod (852) and a spring release button (854). The spring (850) is initially in a compressed state, whereby the advancing rod (852) is disposed in a pre-firing position substantially near the top end of the inserter (800). The spring release button (854) is configured to cause release of the spring (850) in a downward direction (or direction toward the skin (5)). Once the button (854) is pressed, the spring (850) is released, as illustrated in FIG. 15c. Release of the spring (850), causes the advancing rod (852) to apply pressure on the penetrating cartridge (711) thrusting it in a downward direction (or toward the skin (5)) automatically. Movement of the cartridge (711) causes movement of the penetrating member (716) and the cannula (713) toward the skin (5) through the well (310), thereby forcing piercing of the skin (5) and insertion of the penetrating member (716) and the cannula (713) into the subcutaneous compartment (4). After insertion of the cannula (713), the penetrating member (716) can be retracted or removed from the subcutaneous compartment (4).

Figure 15D:
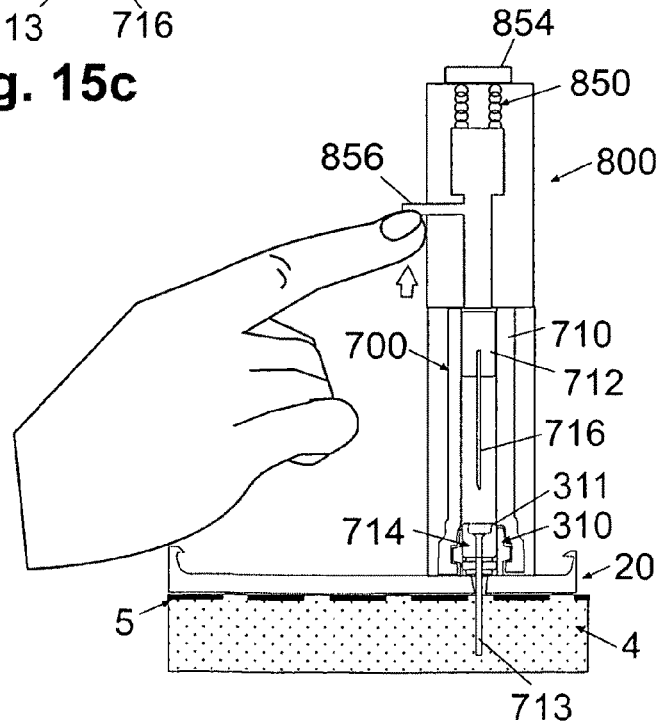

FIG. 15d shows the penetrating member (716) being manually retracted into the protector (710) using a lateral protrusion (856) coupled to the advancing rod (852). The lateral protrusion (856) is configured to move with the advancing rod (852) as it is forced downward during insertion process. To retract the rod (852) into its original position, and thus, retract the penetrating member (716) from the subcutaneous compartment (4), the user can pull on the protrusion (856) in an upward direction (or direction opposite to direction of insertion) and secure the advancing rod (852) in the pre-firing position. Upon removal of the penetrating member (716), the cannula hub (714) remains secured at the well (310), and the cannula (713) remains within the subcutaneous tissue (4). Upon removal of the penetrating member (716), the inserter (800) and the protector (710) can be disconnected from the well (310).

Figure 15E:
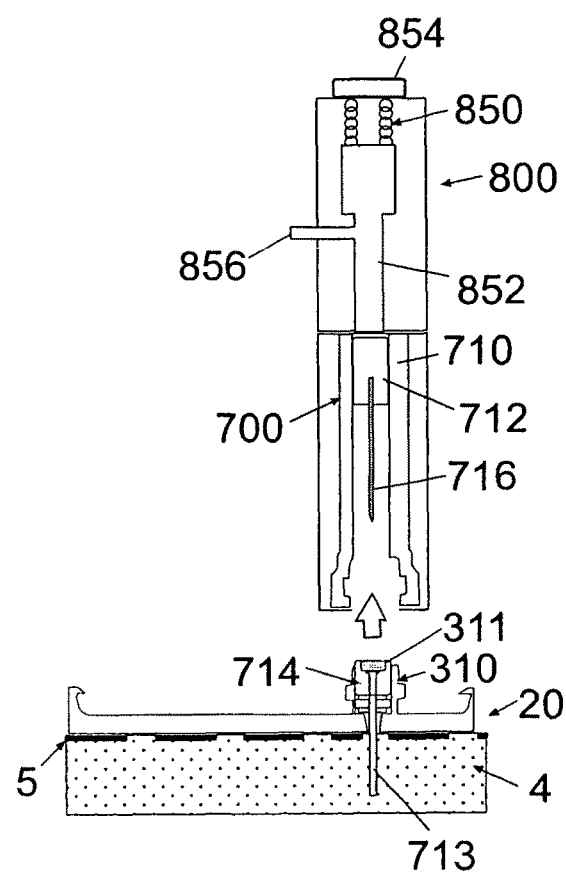

FIG. 15e shows the inserter (800) being disconnected from the cradle unit (20). Upon disconnection the protector (710), now containing only the penetrating member (716), can be unloaded from the inserter (800) and then disposed of. The inserter (800) can be reusable. As can be understood by one skilled in the art, the inserter (800) can be disconnected from the cradle unit (20) after the cannula (713) insertion while the penetrating member (716) remains inside the body. In this case, the user manually removes the penetrating member (716) from the body by holding the grip portion (712) of the penetrating member with his/her fingers and pulling it upwards together with the penetrating member (716). After disconnection of the inserter (800) from the cradle unit (20), the dispensing patch unit is connected to the cradle unit, as previously described with reference to FIGS. 14h-i.

Figure 16A:
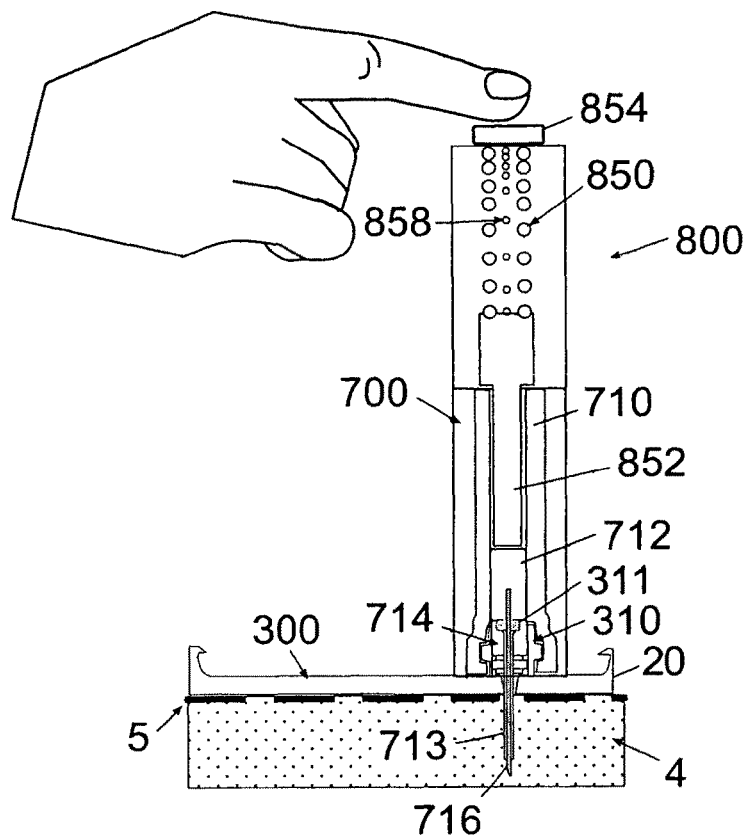
FIGS. 16a-c are cross-sectional views of an exemplary automatic cannula insertion process, according to some embodiments of the present invention.
Figure 16B:
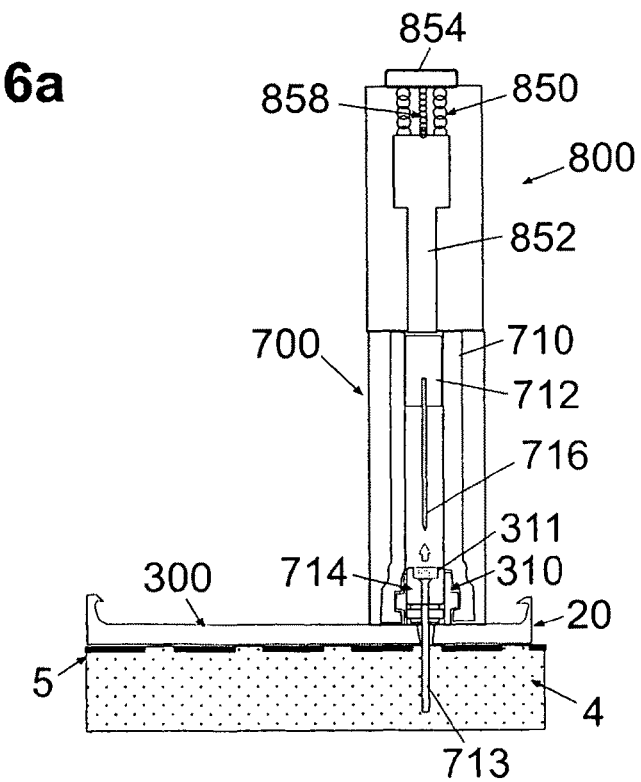
Figure 16C:
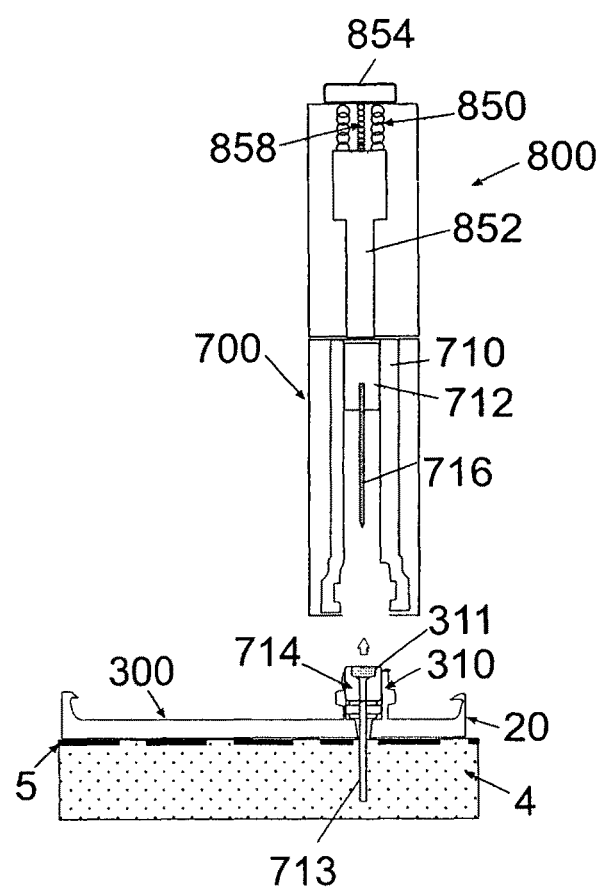

FIGS. 16a-c are cross-sectional views of the cannula cartridge unit during an automatic insertion process. The connection of the inserter (800) to the cradle unit (20) and the insertion of the cannula (713) and penetrating member (716) into the subcutaneous tissue (4) are carried out as previously described with reference to FIGS. 15a-c. However, in this embodiment, the inserter (800) is provided with means for automatically retracting the penetrating member (716). In some embodiments, the inserter (800) includes a retraction spring (858) that can stretch during cannula insertion process, as shown in FIG. 16*a*. The retraction spring (858) can be configured to automatically compress once the penetrating member (716) and the cannula (713) are inserted into the subcutaneous compartment (4) and the cannula hub (714) is secured at the well (310). In some embodiments, the retraction spring (858) can compress upon pressing of the release button (854) or of a separate button (not shown in FIG. 16*a*). FIG. 16*b* shows the penetrating member (716) being retracted into the protector (710) using the retraction spring (858), while the cannula hub (714) is secured at the well (310), and the cannula (713) remains in the subcutaneous tissue (4). FIG. 16*c* shows the inserter (800) being disconnected from the cradle unit (20). The protector (710), now containing only the penetrating member (716), is then unloaded from the inserter (800) and is disposed. After disconnecting the inserter (800) from the cradle unit (20), the dispensing patch unit is connected to the cradle unit, as previously described with reference to FIGS. 14*h-i*.

FIG. 17*a* shows an exemplary pen-like inserter (80) for loading with the cannula cartridge unit (700), according to some embodiments of the present invention. The inserter (80) includes a body portion (810) having an arcuate cross-section to allow loading of the cannula cartridge unit (700) into the inserter (80) from the side of the inserter (80). In some embodiments, the body portion (810) of the inserter (80) can be configured as a tube thereby allowing loading of the cannula cartridge unit (700) in an upward direction through the bottom end of the inserter (80). The body portion (810) includes a bottom open end (849) to allow insertion of the body portion (810) over the well (310), a semi-annular protrusion (812) disposed on the inwardly facing wall and near the top end of the body portion (810). The inserter (80) further includes a firing mechanism coupled to the body portion (810) for inserting the penetrating member and the cannula into the subcutaneous compartment (4), as will be discussed below.

FIG. 17*b* shows loading of the cannula cartridge unit (700) into the inserter (80). As stated above, the unit (700) includes the protector (710) having the opened bottom end (749). The bottom end (749) is placed on the bottom ring-shaped end (849) of the inserter (80), then the protector (710) is pushed into the body portion (810) of the inserter (80) until the semi-annular protrusion (812) is completely engaged with an annular depression (719) disposed on the exterior portion of the protector (710). The protector (710) interlocks with the body portion (810), thereby securing the cannula cartridge unit (700) within the inserter (80). FIG. 17*c* shows the inserter (80) after it has been loaded with the cannula cartridge unit (700) and prior to connecting it to the cradle unit (20).

Figure 18A:
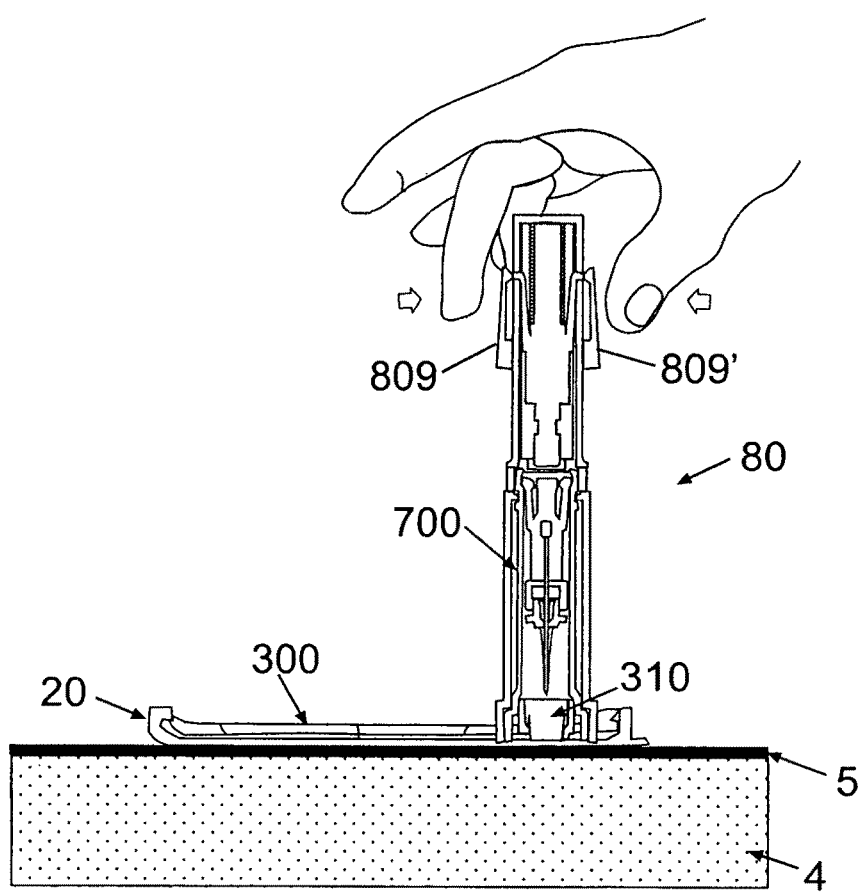

FIGS. 18*a-f* are cross-sectional views of the cannula cartridge unit (700) during the insertion process using the pen-like inserter (80) shown in FIGS. 17*a-c*. FIG. 18*a* shows the inserter (80) after it has been loaded with the cannula cartridge unit (700) and connected to the cradle unit (20) (i.e., placed over the well (310) of the cradle unit (20), as discussed above with regard to FIG. 14*c*). In some embodiments, the inserter (80) includes means for preventing inadvertent or premature firing of the cannula and penetrating member, which can be a cap (not shown in FIG. 18*a*) that is removable from the inserter (80) upon its connection to the cradle unit (20) and prior to initiating the insertion process. To initiate the cannula insertion process, the user employs two lateral triggers (809), (809') disposed on the exterior surface of the inserter (80), as shown in FIG. 18*a*. In some embodiments, the triggers (809) and (809') are used simultaneously to insert the cannula. In some embodiments, there can be a single trigger (809) or more than two triggers (809).

Figure 18B:
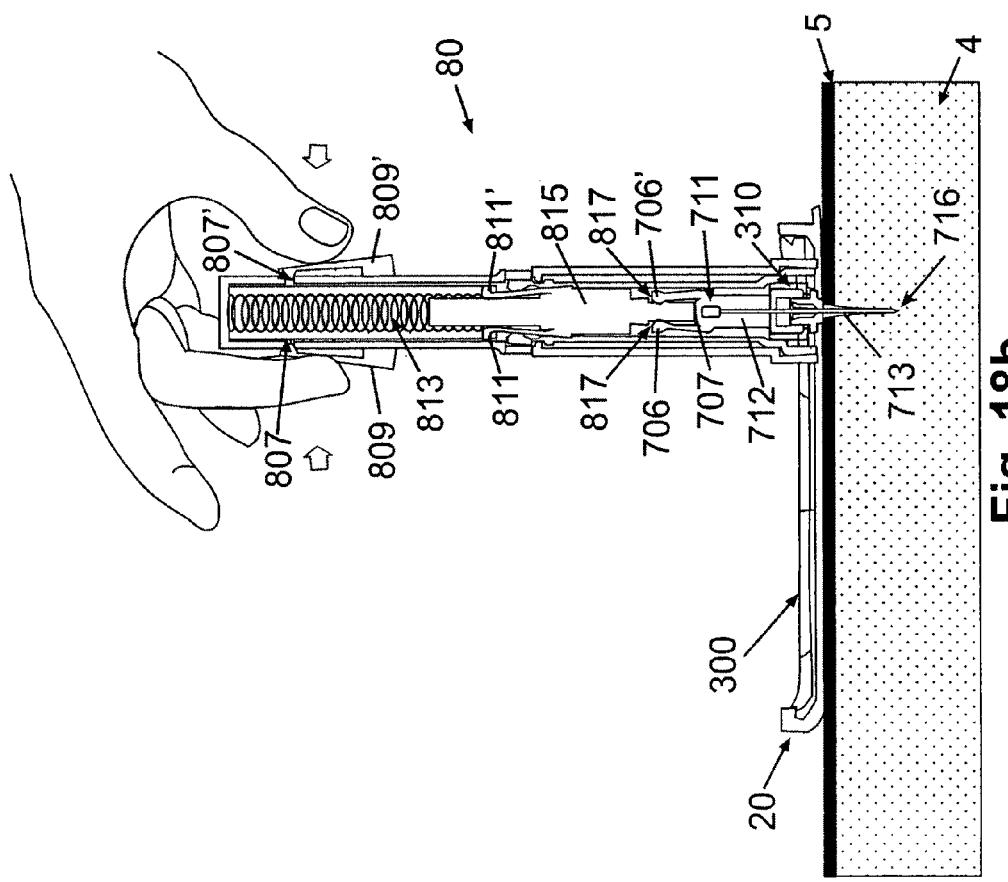

In addition to triggers (809), (809'), the inserter (80) includes a spring (813) disposed inside the inserter (80), rod (815) having an annular depression (817) and being coupled to the spring (813), and spring latches (811), (811') suspended on respective recesses (807), (807') (which are disposed near the top portion of the inserter (80)), as shown in FIG. 18*b*. FIG. 18*b* further shows automatic insertion of the cannula (713) into the subcutaneous tissue (4). Upon pressing (whether simultaneous or not) of the lateral triggers (809), (809'), the spring latches (811), (811') are pushed inwardly, thus releasing them from their respective recesses (807), (807'). The spring (813), which is initially in a compressed loaded state, is released and stretches in a downward direction (or direction toward the skin (5)). As it stretches, the spring (813) pushes on the dedicated rod (815) and forces it to move in a downward direction (or direction toward the skin (5)). When the rod (815) reaches the bottom (707) of the crown-like section of the grip portion (712), spring holding arms (706) forming the crown-like section (only two such arms are shown in FIG. 18*b* and are designated by numerals (706), (706')), are captured by the annular depression (817) provided in the rod (815). As a result, the penetrating cartridge (711) is forced to move in the downward direction toward the well (310). The penetrating member (716) and cannula (713) then penetrate through the well (310) and are inserted into the subcutaneous compartment (4).

FIG. 18*c* shows how the penetrating member (716) is retracted. In some embodiments, the retraction can be carried out manually by the user. After the cannula (713) has been inserted into the subcutaneous tissue (4), the user pushes a lever (803) in an upward direction, where the lever (803) is fixed to the rod (815) and is accessible to the user through a window (804) in the inserter housing (810), as can be seen in FIG. 18*d*. This causes the rod (815) with the penetrating member (716) to retract, and the spring (813) to compress into its pre-firing state. When the spring holding arms (706) reach the top section of the protector (710) having a larger diameter than the body of the protector (710), the arms (706) are released from the annular depression (817) and assume their original position within the protector (710).

The retraction process ends when the spring (813) is returned to its loaded state and the spring latches (811), (811') become suspended in the recesses (807), (807'), respectively. After the penetrating member (716) has been retracted, the cannula hub (714) remains within the well (310). In some embodiments, the well (310) includes spring protrusions (715), (715') to help retain the cannula hub (714) within the well (310).

Figure 18E:
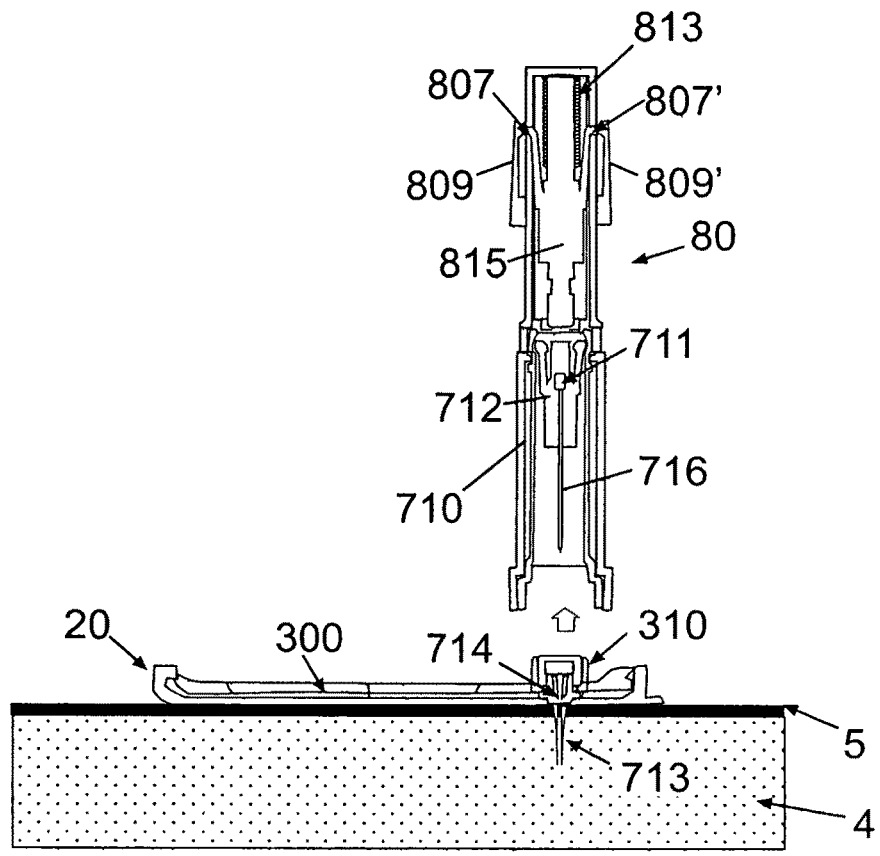

FIG. 18*e* shows the disconnection of the inserter (80) from the cradle unit (20) after the manual retraction process has been completed. At this stage the spring (813) is back in its initial loaded state, and the rod (815) is disconnected from the grip portion (712). After disconnecting the inserter (800) from the cradle unit (20), the dispensing patch unit (not shown in FIG. 18*e*) is connected to the cradle unit (20).

Figure 18F:
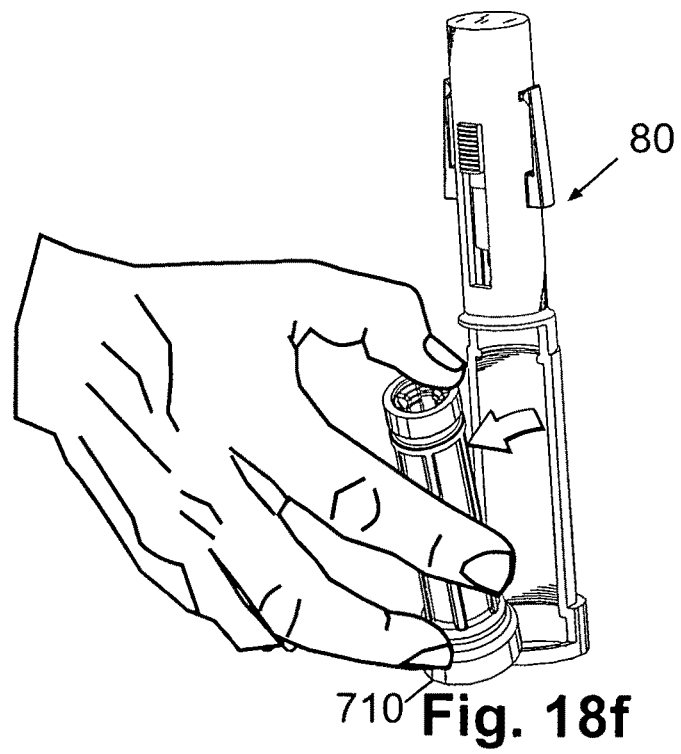

The protector (710) with the penetrating member (716) disposed inside it can then be unloaded from the inserter (80), as shown in FIG. 18*f*, and the unloaded assembly can be disposed.

Figure 19A:
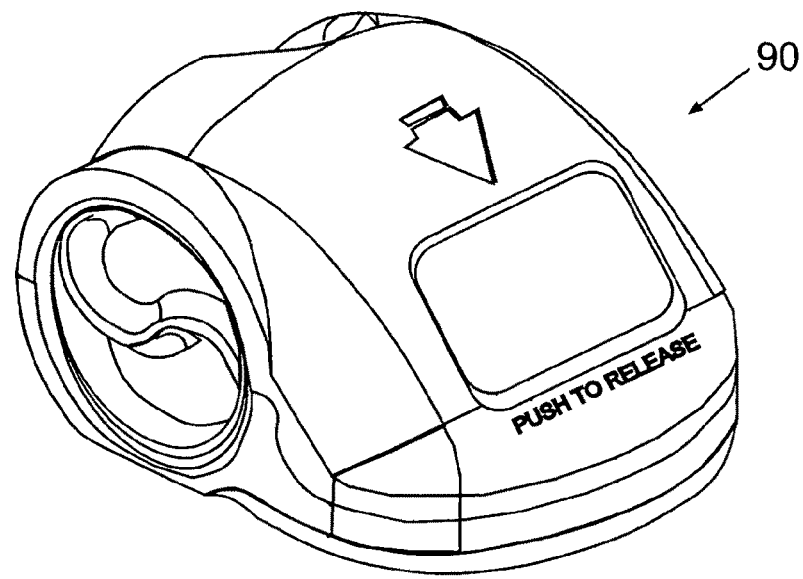
FIG. 19a is a perspective view of an exemplary mouse-like inserter, according to some embodiments of the present invention.

FIG. 19*a* is a perspective view of yet another exemplary inserter (90) that can be configured as a mouse and designed to be loaded with the cannula cartridge unit (not shown in FIG. 19*a*). The inserter (90) can include a release button that allows the user to insert the penetrating member and the cannula (not shown in FIG. 19*a*) into the subcutaneous compartment. The inserter (90) can also include a compartment for insertion of the cannula cartridge unit (700), as will be discussed below. As can be understood by one skilled in the art, the inserter (90) can have any desired shape and is not limited to the inserter (90) shown in FIGS. 19a-h. The inserter (90) shown in these figures is provided for exemplary, non-limiting purposes.

Figure 19B:
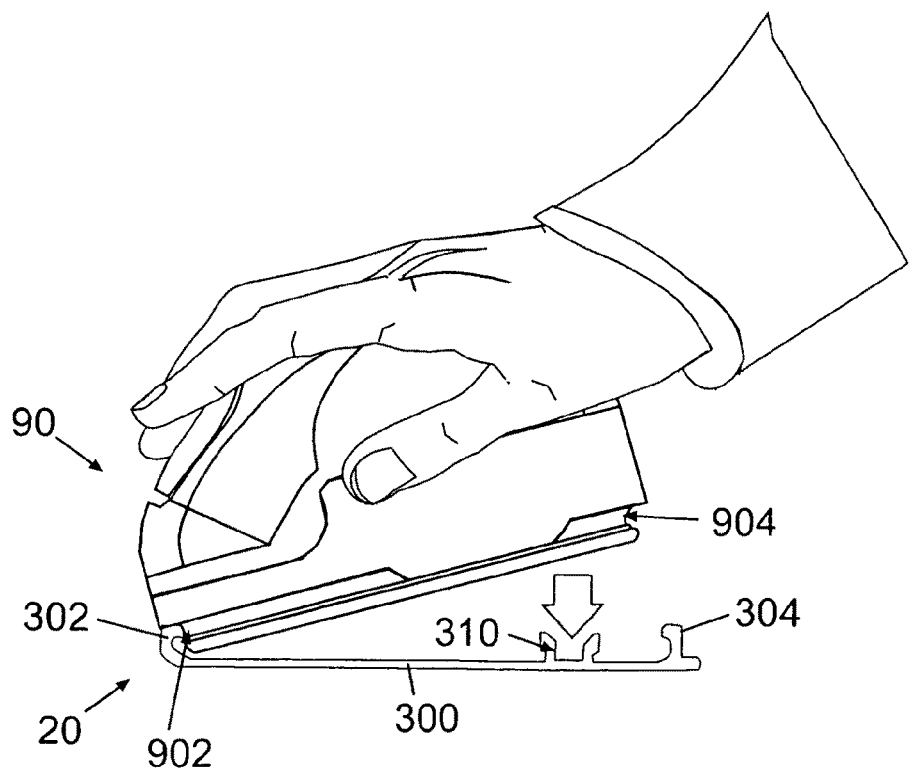
FIGS. 19b-c show exemplary connection of the inserter shown in FIG. 19a to a cradle unit, according to some embodiments of the present invention.
Figure 19C:
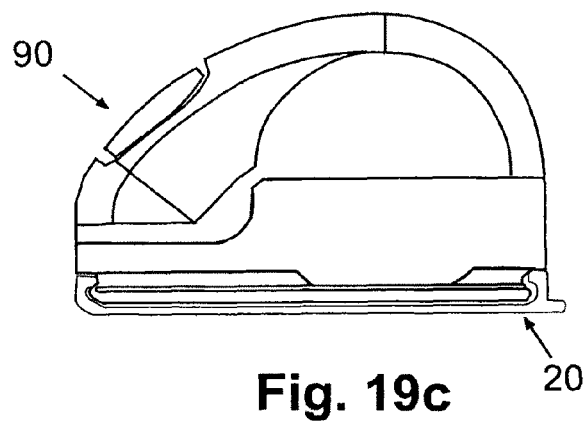

FIG. 19b shows connection of the inserter (90) to the cradle unit (20). In some embodiments, the inserter (90) includes a recess (902) and a notch (904) disposed around the perimeter of the bottom portion of the inserter (90). The inserter (90) is connected to the cradle base (300) by angularly inserting the inserter (90) with the recess (902) mating with a latch (302) of the cradle base (300) and then pushing the inserter (90) in a downward direction and engaging the notch (904) with a latch (304) in a snap-fit arrangement. FIG. 19c is a side view of the inserter (90) being coupled to the cradle unit (20).

Figure 19D:
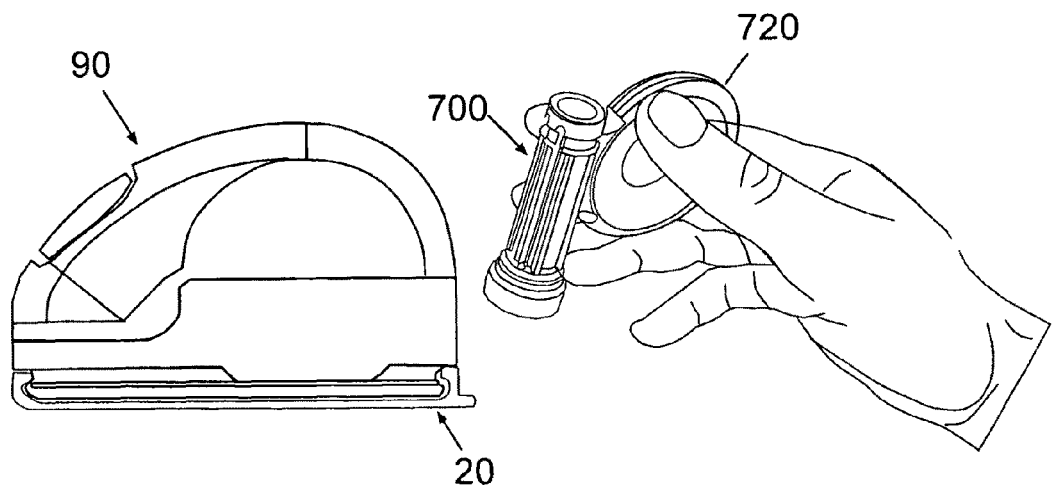
FIGS. 19d-f show loading of the cannula cartridge unit into the inserter shown in FIG. 19a, according to some embodiments of the present invention.
Figures 19E, 19F:
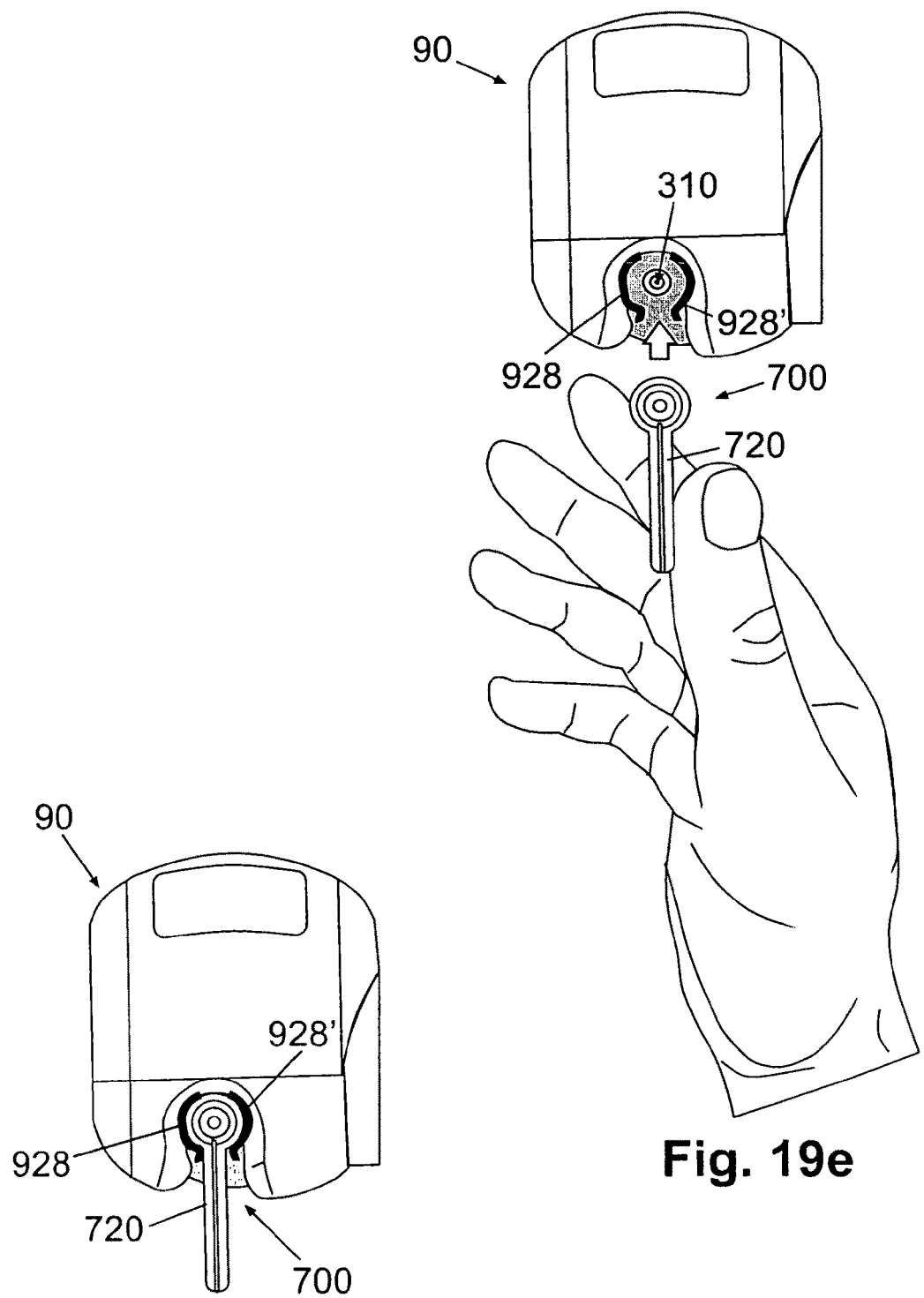

FIGS. 19d-e show the loading of the cannula cartridge unit (700) into the inserter (90). In some embodiments, the unit (700) includes the handle (720), as discussed above with regard to FIGS. 12a-b). To accommodate insertion, the inserter includes spring holders (928), (928') disposed within the opening created in the inserter (90) for insertion of the cannula cartridge unit (700). To insert the unit (700) into the inserter (90), the user grips the cannula cartridge unit (700) by its handle (720), mounts it on the well (310), and then pushes the cannula cartridge unit (700) into the inserter (90) until it is captured by the spring holders (928), (928'), as shown in FIG. 19f. This ensures that the cannula cartridge unit (700) is properly positioned and is ready for the cannula insertion process.

Figure 19G:
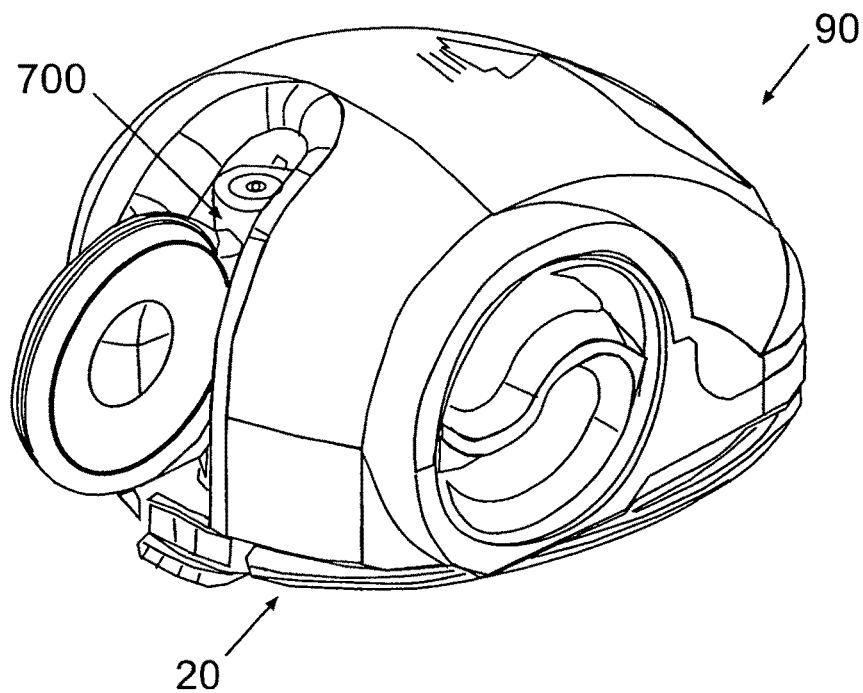
FIG. 19g shows the inserter illustrated in FIG. 19a connected to a cradle unit and loaded with a cannula cartridge unit, according to some embodiments of the present invention.

FIG. 19g is a perspective view of the inserter (90) after it has been connected to the cradle unit (20) and loaded with the cannula cartridge unit (700). As illustrated in FIG. 19g, the inserter is connected to the cradle unit (20) using the latch-recess connection shown in FIGS. 19a-b. The unit (700) is loaded into the opening created in the inserter (90) with the handle (720) protruding away from the unit (700).

Figure 19H:
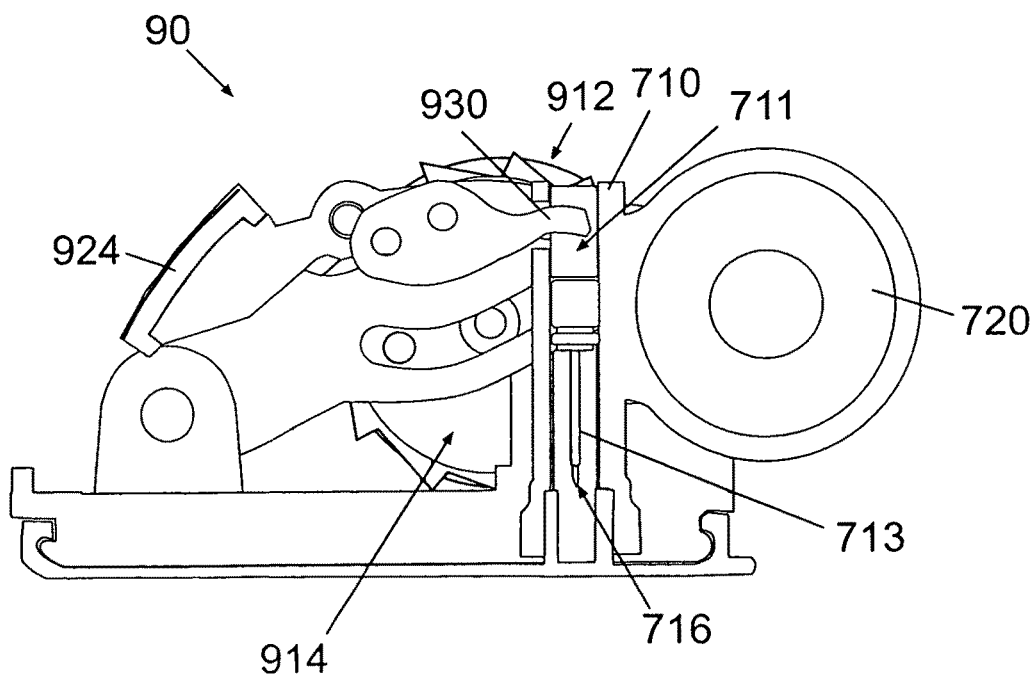

FIG. 19h is a cross-sectional view of the inserter (90). The inserter (90) includes a release button (924) disposed on the outer surface of the inserter's housing, a flywheel (912), a ratchet crank (914), and at least one hook (930). After attaching the cradle unit (20) to the skin (5) of the user the user pushes the release button (924) on the inserter (90). In some embodiments, insertion of the cannula (713) and the penetrating member (716) into the body of the user and retraction of the penetrating member (716) therefrom can be carried out automatically using the spring-loaded flywheel (912) operatively coupled to the ratchet crank (914) and at least one dedicated hook (930), which maintains contact with the penetrating cartridge (711) through the protector's (710) at least one longitudinal slit (not seen). An example of such insertion process is disclosed in the co-owned, co-pending U.S. Provisional Application No. 60/937,214, filed on Jun. 25, 2007, and entitled "Insertion Device for Inserting a Cannula into a Body", the disclosure of which is incorporated herein by reference in its entirety.

Thus it is seen that devices, systems and methods for protecting and concealing needles for use in inserting cannulae and/or sensors into the body of a patient are presented herein. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

All of the foregoing patents, applications, and publications referenced in this specification are hereby incorporated by reference herein in their entireties.

What is claimed is:

1. A cartridge unit for loading into an insertion device, the cartridge unit comprising:
   a protective member comprising a substantially hollow, elongate housing;
   a subcutaneously insertable element; and
   a penetrating member configured to penetrate the skin of the patient to enable subcutaneous insertion of the insertable element,
   wherein:
      the cartridge unit is configured for loading into and unloading out of an insertion device;
      the protective member houses at least the subcutaneously insertable element and the penetrating member prior to the insertable element and penetrating member being protracted from the protective member toward the body of the patient by the insertion device for subcutaneous insertion of the insertable element into the body of the patient,
      the protective member houses at least the penetrating member after the insertable element has been subcutaneously inserted into the body of the patient and the penetrating member has been retracted into the protective member by the insertion device.

2. The cartridge unit according to claim 1, wherein the cartridge unit is devoid of any integrated displacement mechanism.

3. The cartridge unit according to claim 1, further comprising a handle portion extending out from the elongate housing of the protective member.

4. The cartridge unit according to claim 3, wherein the handle portion is configured:
   as a finger-grip for gripping by a user to load the cartridge unit substantially within the insertion device and to unload the cartridge unit therefrom,
   and
   to protrude a distance away from the insertion device when the cartridge unit is loaded therein.

5. The cartridge unit according to claim 1, wherein the protective member is configured to house a variety of different sized and shaped insertable elements.

6. The cartridge unit according to claim 1, wherein:
   the protective member includes a lower open end; and
   the insertable element and penetrating member are protracted through the lower open end to penetrate the skin of the patient.

7. The cartridge unit according to claim 6, wherein the penetrating member is retracted through the lower open end into the protective member after subcutaneous insertion of the insertable element into the body of the patient.

8. The cartridge unit according to claim 1, wherein the elongate housing of the protective member includes at least one window to allow access to the interior of the elongate housing for enabling protraction of the insertable element and penetrating member toward the body of the patient.

9. The cartridge unit according to claim 1, wherein the insertable element comprises a cannula including a cannula hub having a septum for sealing the cannula following retraction of the penetrating member.

10. The cartridge unit according to claim 1, wherein the insertable element is configured to deliver therapeutic fluid into the body of the patient.

11. The cartridge unit according to claim 10, wherein the insertable element further includes sensing means for sensing a bodily analyte.

12. The cartridge unit according to claim 1, wherein the insertable element comprises a sensor for sensing a bodily analyte.

13. The cartridge unit according to claim 10, wherein the therapeutic fluid is insulin.

14. The cartridge unit according to claim 11, wherein the bodily analyte is glucose.

15. The cartridge unit according to claim 1, wherein the protective member includes a lower open end configured for securing to a well portion of a therapeutic fluid delivery system.

16. The cartridge unit according to claim 1, wherein the elongate housing includes at least one slit extending along a length of at least as portion of the elongate housing, the at least one slit configured to receive at least a portion of a displacement mechanism of the insertion device for enabling at least the protraction of the insertable element and penetrating member toward the body of the patient.

17. A method for inserting a subcutaneously insertable element into a body of a patient, the method comprising:
   loading a cartridge unit into an insertion device, wherein the cartridge unit comprises:
      a protective member comprising a substantially hollow, elongate housing,
      a subcutaneously insertable element, and
      a penetrating member configured to penetrate the skin of the patient to enable subcutaneous insertion of the insertable element,
      wherein prior to subcutaneous insertion of the insertable element, the protective member houses at least the insertable element and penetrating member;
   protracting the insertable element and the penetrating member from the protective member via the insertion device ultimately resulting in insertion of the insertable element and the penetrating member into the body of the patient; and
   retracting the penetrating member from the body of the patient via the insertion device, wherein the subcutaneously insertable element is retained in the body of the patient.

18. The method according to claim 17, further comprising unloading the protective member from the insertion device, wherein after the retracting step, the protective member houses at least the penetrating member.

19. The method according to claim 17, wherein at least one of the protracting and retracting steps is performed manually.

20. The method according to claim 17, wherein at least one of the protracting and retracting steps is performed automatically via a spring loaded mechanism included with the insertion device.

21. The method according to claim 17, wherein the protective member is devoid of any integrated displacement mechanism.

* * * * *